United States Patent
Zhang et al.

(10) Patent No.: US 9,763,914 B2
(45) Date of Patent: *Sep. 19, 2017

(54) DEUTERATED BENZOPYRAN COMPOUNDS AND APPLICATION THEREOF

(71) Applicant: GUANGZHOU INSTITUTES OF BIOMEDICINE AND HEALTH, CHINESE ACADEMY OF SCIENCES, Guangdong (CN)

(72) Inventors: Yanmei Zhang, Guangdong (CN); John Jeffrey Talley, Saint Louis, MO (US); Mark G. Obukowicz, Three Lakes, WI (US); Zhengchao Tu, Guangdong (CN); Micky Tortorella, Guangdong (CN); Yican Wang, Guangdong (CN); Jianqi Liu, Guangdong (CN); Yan Chen, Guangdong (CN); Xiaorong Liu, Guangdong (CN); Xin Lu, Guangdong (CN)

(73) Assignee: Guangzhou Institutes of Biomedicine And Health, Chinese Academy of Sciences, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,496

(22) Filed: Jun. 14, 2016

(65) Prior Publication Data
US 2016/0287556 A1  Oct. 6, 2016

Related U.S. Application Data

(63) Continuation of application No. 14/401,600, filed as application No. PCT/CN2012/079968 on Aug. 10, 2012, now Pat. No. 9,371,305.

(30) Foreign Application Priority Data
Jun. 18, 2012 (CN) .......................... 2012 1 0202059

(51) Int. Cl.
| | | |
|---|---|---|
| *A61K 31/353* | (2006.01) | |
| *C07D 311/58* | (2006.01) | |
| *A61K 31/382* | (2006.01) | |
| *A61K 31/47* | (2006.01) | |

(52) U.S. Cl.
CPC .......... *A61K 31/353* (2013.01); *A61K 31/382* (2013.01); *A61K 31/47* (2013.01); *C07D 311/58* (2013.01)

(58) Field of Classification Search
CPC .... A61K 31/353; A61K 31/382; A61K 31/47; C07D 311/58
See application file for complete search history.

(56) References Cited

U.S. PATENT DOCUMENTS

| | | | | |
|---|---|---|---|---|
| 6,034,256 | A | 3/2000 | Carter et al. | 549/456 |
| 6,077,850 | A | 6/2000 | Carter et al. | 514/311 |
| 6,271,253 | B1 | 8/2001 | Carter et al. | 514/432 |
| 6,492,390 | B2 | 12/2002 | Carter et al. | 514/311 |
| 6,806,288 | B1 | 10/2004 | Carter et al. | 514/434 |
| 7,109,211 | B2 | 9/2006 | Carter et al. | 514/311 |
| 7,138,411 | B2 | 11/2006 | Carter et al. | 514/311 |
| 7,259,266 | B2 | 8/2007 | Carter et al. | 549/398 |
| 2005/0148627 | A1 | 7/2005 | Carter et al. | 514/311 |
| 2008/0039473 | A1 | 2/2008 | Gant et al. | 514/252.17 |

FOREIGN PATENT DOCUMENTS

| | | | | |
|---|---|---|---|---|
| CN | 1515566 A | 7/2004 | .......... | C07D 311/66 |
| CN | 1768050 A | 5/2006 | .......... | C07D 311/58 |
| CN | 101547696 A | 9/2009 | .......... | A61K 31/517 |
| WO | WO95/26325 | 10/1995 | .......... | C07B 59/00 |
| WO | WO 98/47890 | 10/1998 | .......... | C07D 311/58 |
| WO | WO 00/23433 | 4/2000 | .......... | C07D 311/58 |

OTHER PUBLICATIONS

Foster, A., (1984). "Deuterium isotope effects in studies of drug metabolism." (*TIPS*)(*Trends in Pharmaceutical Sciences*). 5(12):524-527.
Gierse, J. et al., (2008). "Evaluation of COX-1/COX-2 selectively and potency of a new class of COX-2 inhibitors". *European Journal of Pharmacology.* 588:93-98.
Kowalski, KG., et al (2008). "Modeling and simulation to support dose selection and clinical development of SC-75416, a selective COX-2 inhibitor for the Treatment of acute and chronic pain". *Clinical Pharmacology & Therapeutics*, 83(6):857-866.
Kushner et al., (1999). "Pharmacological uses and perspectives of heavy water and deuterated compounds". *Canadian Journal of Physiology and Pharmacology.* 77(2):79-88.
Wang, J., et al. (2010). "The novel benzopyran class of selective cyclooxygenase-2 inhibitors—part I: The first clinical candidate". *Bioorganic & Medicinal Chemistry Letters.* 20:7155-7158.

(Continued)

*Primary Examiner* — Valerie Rodriguez-Garcia
(74) *Attorney, Agent, or Firm* — Harness, Dickey & Pierce, P.L.C.

(57) ABSTRACT

The present invention discloses deuterated benzopyran compounds having structure features as shown in Formula (I), or pharmaceutically acceptable salts or stereoisomers thereof, or prodrug molecules thereof. With excellent anti-inflammatory and analgesic effects and the capability to inhibit growth of tumor cells, such compounds are novel COX-2 selective inhibitors. The compounds and pharmaceutically acceptable salts thereof disclosed by the present application can be applied in preparing anti-inflammatory and analgesic drugs and drugs for treating or preventing tumors.

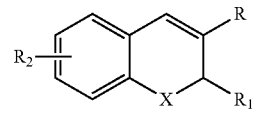

18 Claims, No Drawings

(56) References Cited

OTHER PUBLICATIONS

Wang, J., et al. (2010). "The novel benzopyran class of selective cyclooxygenase-2 inhibitors. Part 2: The second clinical candidate having a shorter and favorable human half-life". *Bioorganic & Medicinal Chemistry Letters.* 20:7159-7163.

Wang, J., et al. (2010). "The novel benzopyran class of selective cyclooxygenase-2 inhibitors. Part III: The three microdose candidates", *Bioorganic & Medicinal Chemistry Letters.* 20:7164-7168.

Xing, L., et al (2011). "Structure-based parallel medicinal chemistry approach to improve metabolic stability of benzopyran COX-2 inhibitors". *Bioorganic & Medicinal Chemistry Letters.* 21:993-996.

Office Action dated Oct. 30, 2015 of U.S. Appl. No. 14/401,600.

ISR dated Mar. 21, 2013 of WO 2013/189121 in PCT/CN2012/079968.

DEUTERATED BENZOPYRAN COMPOUNDS AND APPLICATION THEREOF

CROSS-REFERENCE TO RELATED APPLICATIONS

This application is a continuation application of U.S. Ser. No. 14/401,600, filed Nov. 17, 2014, which is a U.S. National Phase Application of PCT Application No. PCT/CN2012/079968, filed on Aug. 10, 2012, which claims benefit of CN 201210202059.X filed Jun. 18, 2012. The entire disclosures of the applications identified in this paragraph are incorporated herein by references.

TECHNICAL FIELD

The present invention belongs to the field of chemical pharmaceuticals, particularly relates to deuterated benzopyran compounds and application thereof.

BACKGROUND OF THE PRESENT INVENTION

Inflammation, as one of extremely common diseases, severely threatens human health and even brings great impacts on people's living quality. Taking arthritis which is one of the most common chronic diseases as example, it is estimated that there are a total of more than one hundred types, of which osteoarthritis and rheumatoid arthritis are the most common. There are about 355 million people suffering from a variety of joint diseases around the world, of which about 190 million people are osteoarthritis patients and more than 16.5 million people are rheumatoid arthritis patients. It is estimated that there are more than 100 million arthritis patients in China and this number is increasing every year. Although there are already anti-inflammatory and analgesic drugs (belonging to COX-2 inhibitors) available on the market, it is still unable to meet the increasing needs of clinical patients. Accordingly, the research and development of anti-inflammatory and analgesic drugs is still an important direction of drug development.

The traditional nonsteroidal anti-inflammatory drugs (traditional NSAIDs or non-selective NSAIDs) serve as the main anti-inflammatory and analgesic drugs for treating arthritis, including Ibuprofen, Diclofenac sodium, Meloxicam, Nabumetone, Naproxen, etc. Such drugs, on one hand, have anti-inflammatory and analgesic effects, and on the other hand, lead to a variety of severe gastrointestinal adverse reactions complications, for example, epigastric distress, ulcer, gastrointestinal bleeding, perforation and intestinal obstruction and etc. An estimated 60%-80% of such severe gastrointestinal complications have no signal of outbreak. It is speculated by some scholars that, possibly because masking the progress of ulcer by the analgesic effects of such drugs causes the chronic blood loss unconsciously, resulting in aggravation even massive hemorrhage without warning, making it too difficult to prevent or control. It is an unfortunate fact that, in America, about 16,500 people, as high as the number of those died of AIDS, died of gastrointestinal bleeding caused by such traditional non-steroidal anti-inflammatory drugs in 1997, increasing the medical burden on society and family. Therefore, while remaining the excellent anti-inflammation and analgesic effects, developing anti-inflammatory and analgesic drugs capable of decreasing the incidences of severe adverse reactions becomes one of the issues concerned by the medical profession around the world.

The history of nonsteroidal anti-inflammatory drugs (NSAIDs) is a struggle against pain. Specifically, in 1899, the Bayer Company in Germany marketed a variant, acetylsalicylic acid, under the name of aspirin which is the prototype of NSAIDs. Aspirin marked the beginning of the modern anti-inflammatory treatment era, and over the next half-century, served as the main drug for anti-inflammatory treatment. Thereafter, NSAIDs of many types and structures had been successfully developed and marketed. Pyrazolone drugs, appeared in the 1950s, have excellent anti-inflammatory and analgesic effects, but deleterious effects on the bone marrow and other systems. One of indole acetic acid drugs (Indometacin), appeared in the 1960s, had been replaced by Sulindac and Acemetacin marketed in 1980s, due to its severe adverse reactions on gastrointestinal tract, liver and kidney and thus inapplicability to the old and patients suffering from liver, kidney and cardiovascular complications, in spite of excellent anti-inflammatory, analgesic and antipyretic effects. In 1970s, propionic acid drugs for example Ibuprofen, phenylacetic acid drugs for example Diclofenac Sodium, Oxicams for example Proxicam, Anthranilic acid drugs for example Etofenamate appeared. In 1980s, Naproxen was also one of the products marketed. In 1990s, cyclooxygenase-2 (COX-2) selective inhibitors were developed. NSAIDs, which can selectively inhibit the COX-1 and COX-2 enzyme activity, become the mainstream of research and development of anti-inflammatory and analgesic drugs.

Cyclooxygenases (COXs) are primary targets of the nonsteroidal anti-inflammatory drugs (NSAIDs). COXs function as catalytic synthesizing the intermediates, i.e., endoperoxides. (PGG2 and PGH2), of bioactive media such as prostaglandins (PGs) and thromboxane A2 (TXA2). In recent years, it has been found that COXs have two isomers, i.e., COX-1 and COX-2. These two isomers are 60% homologous, but different in both cellular distribution of tissues and biologic functions. PGE2 and PGI2 catalytically synthesized by COX-1 existing in normal tissues have cellular stabilization and protection functions. For example, in the gastric mucosa, PGE2 may promote the secretion of gastric mucus and protect the gastric mucosa. Gastric mucosa damage will be caused in the case of inhibited PGE2 biosynthesis or hyposecretion. COX-2 is cytokine-induced and just exists in the damaged tissues. Prostaglandins catalytically synthesized by COX-2 are inflammatory with high capability of Inducing inflammation and pain. The selective inhibition of COX-2 reduces the prostaglandins synthesized, so that the anti-inflammatory and analgesic effects are realized. As can be seen, the selective inhibition of COX-2 achieves not only the anti-inflammatory and analgesic purposes and also the reduced toxic or side effects to the gastrointestinal tract and kidney. Therefore, seeking COX-2 selective inhibitors is a major direction for the research and development of a new generation of NSAIDs. The fundamental research of COX-2 and the clinical application and safety assessment of COX-2 selective inhibitors become the common concerns of many subjects.

Cyclooxygenase (COX) protein was once believed to be produced by a single gene. COX is fundamentally composed of three independently folded units, i.e., epidermal growth factor domain, membrane binding domain and enzymatic activity domain. In 1990, the second isoenzyme of COX, which is different from the "typical" COX in both structure and function, was found in various cells. Hence, the typical COX as constitutive enzyme was named as COX-1 and the other COX as inducible enzyme was named as COX-2. The protein of COX-2 is made up of 604 amino acids. According to the well known crystal structure of COX, by the sequencing of COX-2, the difference in active sites between COX-2 and COX-1 is determined. The 523rd amino acid of COX-2 is valine, the structure of which is smaller than the leucine in a corresponding site of COX-1. Another difference lies in that there is a small recess which is produced in a different position on the 384th side-chain of leucine between COX-1 and COX-2. This difference exists because there are large non-steroidal anti-inflammatory drugs (NSAIDS) binding sites, so that the inhibition dedicated to COX-2 from the substrate is realized by enhancing the affinity with respect to the occupation of the macromolecule substrate. The discovery of COX-2 provides important theoretic basis for the development and use of the COX-2 selective inhibitors.

Most scholars believe that the pharmacological effects and adverse reactions of NSAIDs depend on the level of inhibition to COX-1 and COX-2. Specifically, the level of inhibition to COX-1 is higher, the adverse reactions on the digestive tract, kidney and etc. are severer; and, the level of inhibition to COX-2 is higher, the anti-inflammatory and analgesic effects are greater. Coxibs NSAIDs (COX-2 selective inhibitors) represented by Celecoxib, Rofecoxib and Valdecoxib are emerged in this context, with less adverse reactions on the gastrointestinal tract as their major advantage. It is generally recognized that COX-2 selective inhibitors have less adverse reactions on the gastrointestinal tract and less toxicity to the kidney than common non-steroidal anti-inflammatory drugs as they do not work on COX-1 and have no impact on the synthesis of PGI2 which may protect the gastrointestinal tract and the kidney. The COX-2 selective inhibitors, for example, Celecoxib, have an efficacy on chronic inflammation approximating to NSAIDs. However, they have quick analgesic effects slightly weaker when compared with ibuprofen and will cause a high incidence of cardiovascular side-effects. Over time, more adverse reactions have been further recognized, including: the recognition of adverse cardiovascular events caused as the COX-2 selective inhibitors have no inhibition to COX-1 and thromboxane A2 (TXA2) on the platelets.

A consensus has been reached on the clinical research of the COX-2 inhibitors. Specifically, due to different chemical structures, drugs even of the type may be completely different in safety; and some COX-2 inhibitors may even have cardiovascular protection function. The most important is that COX-2 selective inhibitors can produce more benefits than the traditional non-steroidal anti-inflammatory drugs, particularly in the reduction of gastrointestinal side effects. Hence, the search and development of anti-inflammatory and analgesic drugs still focus on COX-2 selective inhibitors.

Benzopyran compounds themselves, as novel COX-2 selective inhibitors, have carboxyl groups which will not be reacted with the hydrophobic groups in the active sites of COX-2. Benzopyran drug candidates, differentiated from diarylheterocyclicoxib compounds, have the same efficacy and selectivity as the diarylheterocyclicoxib compounds and show the capability to reduce the tactile allodynia in the rat model of neuropathic pain. It has been proved that benzopyran compounds have better treatment effects on inflammation and pain than the existing coxib compounds, and such compounds have a potential kidney protection function, thereby reducing the possibility of hypertension caused by the internal structure and the pharmacological and physiological properties. Hence, the development of such COX-2 selective inhibitors as anti-inflammatory and analgesic drugs is of great significance.

SUMMARY OF THE PRESENT INVENTION

Accordingly, an objective of the present invention is to provide novel deuterated benzopyran compounds.

The technical solution will be described specifically as below.

Deuterated benzopyran compounds having structure features as shown in Formula (I), or pharmaceutically acceptable salts or stereoisomers thereof, or prodrug molecules thereof:

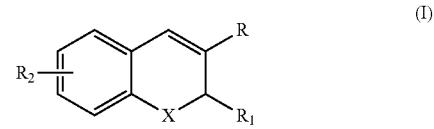

X is optionally selected from O, S or $NR^a$;
$R^a$ is optionally selected from:
1) H;
2) $C_1$-$C_3$ alkyl;
3) $C_3$-$C_6$ Cycloalkyl;
4) $C_1$-$C_3$ alkyl substituted by one or two halogen; and
5) aryl.
R is optionally selected from:
1) carboxyl;
2) acylamino;
3) alkysulfonyl; and
4) alkoxycarbonyl;
$R_1$ is optionally selected from:
1) haloalkyl;
2) alkyl;
3) aralkyl; and
4) cycloalkyl;
$R_2$ is selected from one or more of the following groups to form deutero-naphthyl:
1) deuterium;
2) halogen;
3) alkyl or deutero-alkyl;
4) aralkyl or deutero-aralkyl;
5) alkoxy or deutero-alkoxy;
6) aryloxy or deutero-aryloxy;
7) heteroaryloxy or deutero-heteroaryloxy;
8) arylalkoxy or deutero-arylalkoxy;
9) heteroarylalkoxy or deutero-heteroarylalkoxy;
10) haloalkoxy or deutero-haloalkoxy;
11) haloalkoxy or deutero-haloalkoxy;
12) amino or deutero-amino;
13) substituted amino or substituted deutero-amino;
14) sulfamidyl or deutero-sulfamidyl;
15) substituted sulfamidyl or substituted deutero-sulfamidyl;
16) carbonyl;
17) substituted carbonyl or substituted deutero-carbonyl; and $R_2$ reacts with benzene to form deutero-naphthyl.
In some of embodiments, X is O or S;
R is selected from carboxyl, $C_1$-$C_3$ Cyclocarbonyl, aryl-substituted $C_1$-$C_3$ Cyclocarbonyl and $C_1$-$C_3$ alkoxycarbonyl; and
$R_1$ is selected from haloalkyl, cycloalkyl and phenyl.
$R_2$ is selected from one or more of the following groups to form deuterated compounds:
1) deuterium;
2) halogen;

3) alkyl or deutero-alkyl;
4) alkoxy or deutero-alkoxy;
5) haloalkyl or deutero-haloalkyl;
6) alkylamino or deutero-alkylamino;
7) nitryl;
8) alkylated sulfamidyl or deutero-alkylated sulfamidyl;
10) acyl or deutero-acyl;
11) aryl or deutero-aryl; and
R2 reacts with benzene to form deutero-naphthyl.

In some of embodiments, X is O or S; R is carboxyl; $R_1$ is rifluoromethyl or pentafluoromethyl;

R2 is optionally selected from one or more groups to form deuterated compounds:
1) deuterium;
2) halogen;
3) methyl, ethyl, isopropyl, tert-butyl, or, deutero-methyl, deutero-ethyl, deutero-isopropyl, deutero-tert-butyl;
4) trifluoromethyl, trifluoromethoxy;
5) haloalkyl or deutero-haloalkyl;
6) alkylated sulfamidyl or deutero-alkylated sulfamidyl;
7) methylsulfonyl or deutero-methylsulfonyl;
8) aroyl or deutero-aroyl;
9) aryl or deutero-aryl; and
R2 reacts with benzene to form deutero-naphthyl.

In some of embodiments, the X is O; R is carboxyl; $R_1$ trifluoromethyl;

R2 is optionally selected from one or more groups to form deuterated compounds:
1) deuterium;
2) halogen;
3) methyl, ethyl, isopropyl, tertbutyl, or, deutero-methyl, deutero-ethyl, deutero-isopropyl, deutero-tert-butyl;
4) trifluoromethyl, trifluoromethoxy;
5) haloalkyl or deutero-haloalkyl; and
6) aryl or deutero-aryl.

In some of embodiments, the compound is selected from:
6-(methyl-D3)-2-(trifluoromethyl)-2H-chromence-3-carboxylic acid;
ethyl 8-(ethyl-D5)-6-(trifluoromethoxy)-2-(trifluoromethyl)-2H-chromene-3-carboxylic acid;
6-chloro-5,7-(dimethyl-D6)-2-(trifluoromethyl)-2H-chromene-3-carboxylic acid;
6-bromo-5,7-(dimethyl-D6)-2-(trifluoromethyl)-2H-chromene-3-carboxylic acid;
6-chloro-8-(methyl-D3)-2-(trifluoromethyl)-2H-chromene-3-carboxylic acid;
6-bromo-8-(methyl-D3)-2-(trifluoromethyl)-2H-chromene-3-carboxylic acid;
8-chloro-6-(methyl-D3)-2-(trifluoromethyl)-2H-chromene-3-carboxylic acid;
6,8-dibromo-5,7-(dimethyl-D6)-2-(trifluoromethyl)-2H-chromene-3-carboxylic acid;
7-(methyl-D3)-2-(trifluoromethyl)-2H-chromene-3-carboxylic acid;
7-(ethyl-D3)-2-(trifluoromethyl)-2H-chromene-3-carboxylic acid;
6-chloro-7-(methyl-D3)-2-(trifluoromethyl)-2H-chromene-3-carboxylic acid;
8-(1-methylhexyl-D15)-2-(trifluoromethyl)-2H-chromene-3-carboxylic acid;
6-chloro-8-(methyl-D3)-2-(trifluoromethyl)-2H-chromene-3-carboxylic acid;
6-chloro-7-(1,1-dimethylhexyl-D17)-2-(trifluoromethyl)-2H-chromene-3-carboxylic acid;
6-chloro-8-(1-methylhexyl-D15)-2-(trifluoromethyl)-2H-chromene-3-carboxylic acid;
7-(1-methylhexyl-D15)-2-(trifluoromethyl)-2H-chromene-3-carboxylic acid;
6-chloro-7-(hexyl-D13)-2-(trifluoromethyl)-2H-chromene-3-carboxylic acid;
8-(hexyl-D13)-2-(trifluoromethyl)-2H-chromene-3-carboxylic acid;
7,8-(dimethyl-D6)-2-(trifluoromethyl)-2H-chromene-3-carboxylic acid; and
6-chloro-8-(hexyl-D13)-2-(trifluoromethyl)-2H-chromene-3-carboxylic acid.

Another objective of the present invention is to provide an application of the deuterated benzopyran compounds described above, or pharmaceutically acceptable salts or stereoisomers thereof, or prodrug molecules thereof, in preparing anti-inflammatory and analgesic drugs or preparing drugs for preventing or treating tumors.

The technical solution will be described specifically as below.

Disclosed is an application of the deuterated benzopyran compounds described above, or pharmaceutically acceptable salts or stereoisomers thereof, or prodrug molecules thereof, in preparing anti-inflammatory and analgesic drugs or preparing drugs for preventing or treating tumors.

In some of embodiments, the inflammation mainly comprises rheumatoid arthritis, gouty arthritis, osteoarthritis and rachitis, further comprises one of systemic lupus erythematosus, psoriasis, eczema, skin inflammation and postpartum inflammation, bowel disease, gastritis, irritable bowel syndrome, headache, exarteritis, thyroiditis, aplastic anemia, retinitis, conjunctivitis, retinopathy, uveitis, hemeralopia, acute ocular tissue injury, viral infection and cystic fibrosis, allergic rhinitis, postpartum pain, toothache, muscle pain, cancer pain, aneurysm, coronary plaque inflammation, inflammation caused by bacteria, inflammation caused by viruses, inflammation caused by surgery, ocular vascular hyperplasia, retinal vascular hyperplasia and gastriculcer.

In some of embodiments, the tumor is one of hemangioma, endometriosis, gastrointestinal stromal tumor, histiocytic lymphoma, non-small cell lung cancer, small-cell lung cancer, lung adenocarcinoma, squamous cell carcinoma, pancreatic cancer, breast cancer, prostate cancer, liver cancer, skin cancer, squamous cell carcinoma, nasopharyngeal carcinoma and leukemia.

Another objective of the present invention is to provide pharmaceutical compositions.

The technical solution will be described specifically as below.

Disclosed are pharmaceutical compositions composed of the deuterated benzopyran compounds described above, or pharmaceutically acceptable salts or stereoisomers thereof, or prodrug molecules thereof, and pharmaceutically acceptable carriers.

When any variable (e.g., R1, R, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

The term "deuterium" as used herein is intended to mean a single deuterium atom, where the deuterium radicals are attached onto the carbon atoms or oxygen atoms to form deuterted compounds. As used herein, the terms "alkyl" and "alkylene" are intended to include both branched and straight-chain saturated aliphatic hydrocarbon groups having the specified number of carbon atoms. For example, "$C_1$-$C_5$" as in "$C_1$-$C_5$ alkyl" is defined to include groups having 1, 2, 3, 4 or 5 carbon atoms in a linear or branched arrangement. For example, "$C_1$-$C_5$ alkyl" specifically includes methyl, ethyl, n-propyl, isopropyl, n-butyl, t-butyl, isobutyl, pentyl, etc. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethylcyclobutyl, 2-ethyl-cyclopentyl, cyclohexyl, etc.

"Alkoxy" represents either a cyclic or non-cyclic alkyl group of indicated number of carbon atoms attached through an oxygen bridge. "Alkoxy" therefore encompasses the definitions of alkyl and cycloalkyl above.

The term "aryl" as used herein is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heteroaryl" as used herein represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furyl, thienyl, benzothiophenyl, benzofuryl, quinolyl, isoquinolyl, oxazolyl, isoxazoyl, indolyl, pyrazinyl, pyridazinyl, pyridyl, pyrimidinyl, pyrrolyl and tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Sulfamine as used herein is "—SO2NH2-". As appreciated by those skilled in the art, "halo" or "halogen" as used herein is intended to include chlorine, fluorine, bromine and iodine.

Unless specifically defined, alkyl, cycloalkyl, aryl, heteroaryl, heterocyclic substituents may be or not substituted. For example, ($C_1$-$C_6$) alkyl may be substituted by one, two or three substitutents selected from OH, halogen, alkoxyl, dialkylamino, or heterocyclic such as morpholinyl, piperidinyl.

Included in the present invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the present invention may be synthesized from the compounds of the present invention which contain a basic or acidic moiety by conventional chemical methods. Generally, the salts of the basic compounds are prepared either by on exchange chromatography or by making the free base react with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of the present invention include the conventional non-toxic salts of the compounds of this invention as formed by making a basic instant compound react with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as argi-nine, betaine caffeine, choline, N,N1-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

It will be noted that, the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The present invention relates to deuterated benzopyran compounds having structure features as shown in Formula (I). With excellent anti-inflammatory and analgesic effects and the capability to inhibit growth of tumor cells, such compounds are novel COX-2 selective inhibitors. The compounds and pharmaceutically acceptable salts thereof disclosed by the present application can be applied in preparing anti-inflammatory and analgesic drugs and drugs for treating or preventing tumors.

DETAILED DESCRIPTION OF THE PRESENT INVENTION

The compounds of the present invention may be prepared by using the following reactions besides the methods which have been published in articles or well validated in the experimental procedures. Therefore, the synthetic solutions below are just illustrative and not intended to limit the compounds or any specific substituent. The number of the substituents in the solution does not need to comply with the number specified in the Claims. Furthermore, for clear, the Formula (I) showing a single substitution may allow compounds with multiple substituents.

Solutions

As shown in Solution A, compounds in Formula (I) may be synthesized by three steps by using deuterated phenol as the starting material.

Solution A

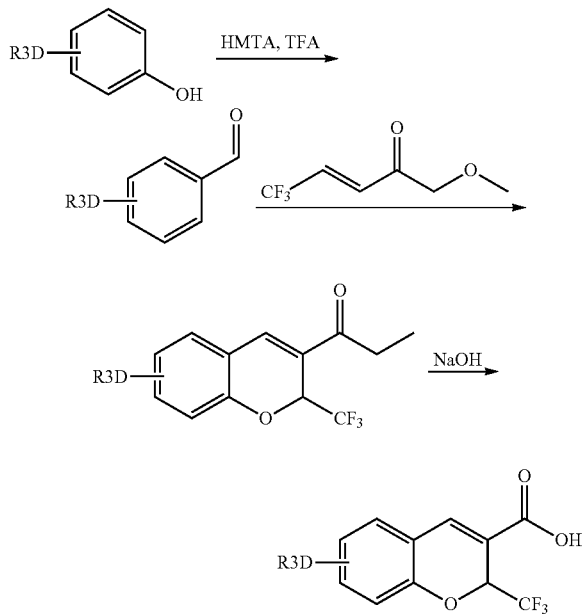

The compounds and pharmaceutically acceptable salts thereof designed in the present application may be used with other traditional anti-inflammatory drugs both available or under development, for example, drugs such as steroid anti-inflammatory drugs, non-steroid anti-inflammatory drugs, iNOS inhibitors, LTB4 receptor stimulants and LTA4 hydrolase inhibitors, to enhance the anti-inflammatory and analgesic effects, or, may be used with antibiotics, alkylated drugs, antimetabolites, hormone drugs, immuno drugs, interferon drugs and some other combinations of drugs to enhance the treatment or inhibition effects to tumors.

Administration and Dose Ranges

Based on the standard pharmaceutical technology, the compounds of the present invention may be administrated alone or in pharmaceutical combinations with pharmaceutically acceptable receptors, accessories or diluents to mammals, preferably human beings, for example, by oral, subcutaneous. Intraperitoneal, intravenous, rectal, topical, ocular, pulmonary, nasal and parenteral.

When compounds of Formula (I) are used in cancer patients for anti-inflammatory and analgesic purposes or treatment, the oral dose is 0.1-500 mg/day/kg administrated in a single dose daily, or in two, three, four or some other times a day, or in sustained release forms. For most large mammals, the dose is preferably 0.1-1500 mg/day/kg, more preferably 0.5-100 mg/day/kg. For patients of average weight of 70 kg, the daily dose is 1-100 mg/day/kg. For some particularly highly active compounds, the daily dose for adults may be as low as 0.1 mg/day.

Preparations:

The pharmaceutical compositions containing active ingredients may be in a form suitable for oral administration, for example, tablets, lozenges, aqueous or oily suspensions, dispersible powders or granules, emulsions, hard or soft capsules, or syrups or elixirs. Compositions intended for oral administration may be prepared according to any method known in the art of the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, microcrystalline cellulose, sodium crosscarmelose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed. The dose of tablets may be 0.1 mg/tab, 0.2 mg/tab, 0.25 mg/tab, 0.5 mg/tab, 1 mg/tab, 2 mg/tab, 5 mg 10 mg/tab, 25 mg/tab, 50 mg/tab, 100 mg/tab and 250 mg/tab. The dose of other forms, such as capsulates, may be referenced similarly.

Formulations for oral use may also be presented as hard gelatin capsules where the active Ingredients are mixed with inert solid diluents, for example, calcium carbonate, calcium phosphate or kaolin, or, as soft gelatin capsules where the active ingredients are mixed with water soluble carriers such as polyethyleneglycol or an oil medium, for example peanut oil, liquid paraffin or olive oil.

Aqueous suspensions contain active materials in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents such as sucrose, saccharin or aspartame.

Oily suspensions may be formulated by suspending the active ingredients in a vegetable oil, for example arachis oil, olive oil, sesame oil or coconut oil, or in mineral oil such as liquid paraffin. The oily suspensions may contain thickening agents, for example beeswax, hard paraffin or cetyl alcohol. Sweetening agents such as those set forth above and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredients in admixture with dispersing or wetting agent, suspending agent and one or more preservatives. Suitable dispersing or wetting agents and suspending agents have been exemplified by those already mentioned above. Additional excipients, for example sweetening, flavoring and coloring agents, may also be present. These compositions may be preserved by the addition of an anti-oxidant such as ascorbic acid.

The pharmaceutical compositions of the present invention may also be in a form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain demulcents, preservatives, flavoring agents, coloring agents and antioxidants.

The pharmaceutical compositions may be in a form of sterile injectable aqueous solutions. Among the acceptable carriers and solvents that may be employed are water, Ringer's solution and isotonic sodium chloride solution.

The sterile injectable preparation may also be a sterile injectable oil-in-water microemulsion where the active ingredients are dissolved in the oily phase. For example, the active ingredients may be first dissolved in a mixture of soybean oil and lecithin. The oil solution is then introduced into a water and glycerol mixture and processed to form microemulsions.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An embodiment of such a device is the Deltec CADD-PLUS™ model 5400 intravenous pump.

The pharmaceutical compositions may be in a form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, nonvolatile oils are conventionally employed as a solvent or suspending medium. For this purpose, any bland nonvolatile oil may be employed including synthetic mono- or diglycerides. In addition, fatty acids such as oleic acid find use in the preparation of injectables.

Compounds of Formula I may also be administered in the form of suppositories for rectal administration of the drug. These compositions may be prepared by mixing the drug with a suitable non-irritating excipient which is solid at normal temperature but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of Formula I are employed. (For purposes of this application, topical application shall include mouth washes and gargles.)

The compounds of the present invention may be administered in intranasal form via topical use of suitable intranasal carriers and delivery devices, or via transdermal routes, using those forms of transdermal skin patches well known to those of ordinary skill in the art. To be administered in the form of a transdermal delivery system, the dose administration will, of course, be continuous rather than intermittent throughout the dose regimen. The compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When the compounds of the present invention are administered to a human subject, the daily dose will normally be determined by the prescribing physician with the dose generally varying according to the age, weight, sex and response of the individual patient, as well as the severity of the patient's symptoms.

Metabolites and Prodrugs:

The metabolites of the compounds and pharmaceutically acceptable salts thereof disclosed in the present invention, and prodrugs that may be converted to the compounds and pharmaceutically acceptable salts thereof disclosed in the present invention are encompassed in the claims of the present application.

Combined Therapy:

The compounds of Formula I may be used in combination with other drugs which have been known to be useful in the treatment or amelioration of the diseases or similar diseases. In the combined administration, such other drugs may be administered, by a route administration and in a dose commonly used, and contemporaneously or sequentially with the compounds of Formula I. When the compounds of Formula I are used contemporaneously with one or more other drugs, a pharmaceutical composition containing one or more other known drugs and the compounds of Formula I is preferred. The combined therapy also includes therapies in which the compounds of Formula I and one or more other known drugs are administered on overlapping schedules. When used in combination with one or more other drugs, the compounds of Formula I and the other known drugs may be used in a lower dose than when they are used alone.

Drugs or active ingredients which may be used in combination with the compounds of Formula I include but are not limited to:

1) traditional steroid anti-inflammatory and analgesic drugs, for example, Dexamethasone, Diethyistilestrol;

2) non-steroid anti-inflammatory and analgesic drugs, for example, Diclofenac, Chlorfenamic Acid, Analgin, Amino beaver, Aspirin, Butazodine, Piroxicam, Indometacin, Naproxen, Ibuprofen, Piroxicam, Celecoxib, Nabumetone, Ketoprofen, Ketorolac, Tetraclofenamic acid, Sulindac, Magnesium salicylate, Natrium salicylicum, Magnesium choline salicylate, Diflunisal, Sasapyrine;

3) LTB$_4$ receptor antagonist, for example, CGS-25019C, ETH-615, T-0757, LY-213024, LY-210073, LY223982, LY233469, ONO-LB457, ONO-4057, ONO-LB-448, SC-53228, SC-41930, SC-50605, SC-51146, SB-209247;

4) 5-LO inhibitors, for example, A-76745, 78773, ABT761, CMI-392, E-3040. ML-3000, PF-5901, EF-40, F-1322, ML-3000, R-840;

5) iNOS inhibitors;

6) LTA4 hydrolase inhibitors, for example, RP-64966;

7) Mu receptor antagonist;

8) Kappa receptor antagonist;

9) neurokinins receptor antagonist;

10) antibiotic anticancer drugs, for example, Taiho 4181-A, Takeda TAN-868A, Fujisawa FK-973, Bristol-Myers BL-6859, KM-5539, KT-5432;

11) alkylation of anticancer drugs, for example, Shionogi 254-S, Sanofi CY-233, Degussa D-19-384, NCI NSC-164395, NCI NSC-342215, Proter PTT-119;

12) antimetabolite drugs, for example, Lilly DATHF, Lilly LY-188011, Lilly LY-264618, NCI NSC-127716, NCI NSC-164880, NCI NSC-39661, NCI NSC-612567;

13) hormonal anticancer drugs;

14) immune anticancer drugs;

15) interferon anticancer drugs;

16) radioprotector, for example, AD-5, 1-201, MM-159, WR-151327, FUT-187;

17) some other mixed anticancer drugs, for example, Biotec AD-5, Kyorin AHC-52, Ajinomoto CDAF, Chemex CHX-100, Merz D-609;

The above combinations include combinations of the compounds of Formula I not only with one of drugs mention above, but also with two or more than two of these drugs.

The present invention will be further explained as below by embodiments.

Embodiment 1

6-(methyl-D3)-2-(trifluoromethyl)-2H-chromence-3-carboxylic acid

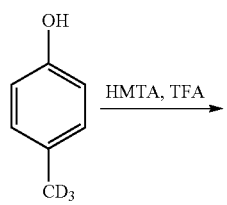

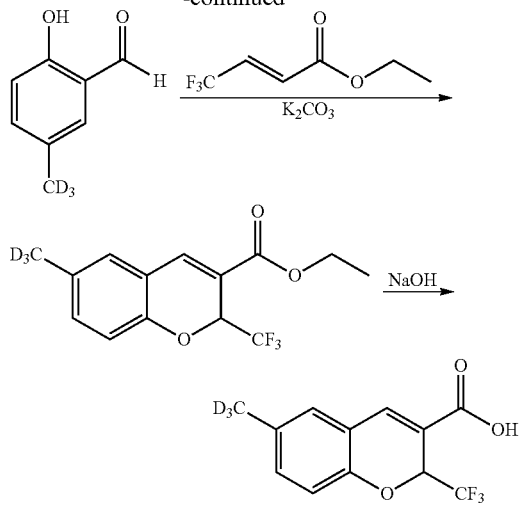

Step 1: 2-hydroxy-5-(methyl-D3)-benzaldehyde

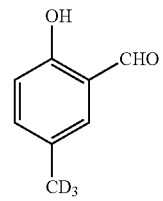

4-(methyl-D3)-phenol (0.90 g, 8.1 mmol) was dissolved into trifluoroacetic acid (6 mL) and then slowly added with hexamethylenetetramine (1.3 g, 9.6 mmol). The system was reacted at 80° C. for 1 hr, cooled to room temperature, added with water (6 mL) and then stirred for 0.5 hrs. At the end of reaction, saturated sodium bicarbonate solution was added and extracted with ethyl acetate, and the organic phase was washed with brine, dried and evaporated in vacuum to obtain 0.30 g of the product (27%) by column chromatography.

$^1$HNMR (400 MHz, d-CDCl$_3$), δ 10.74 (s, 1H), 9.77 (s, 1H), 7.24 (d,2H), 6.80 (s, 1H)

Step 2: 6-(methyl-D3)-2-(trifluoromethyl)-2H-chromence-3-carboxylate

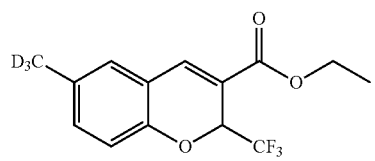 [SMILES: [2H]C([2H])([2H])c1ccc2c(c1)C=C(C(=O)OCC)C(C(F)(F)F)O2]

The resulting product (0.25 g, 1.8 mmol) from step 1, anhydrous K$_2$CO$_3$ (0.25 g, 1.8 mmol) and ethyl 4,4,4-trifluorocrotonate (1.2 g, 7.2 mmol) were mixed in DMF (10 mL), and then the system was heated to 85° C. for reaction for 2 hrs. At the end of reaction, the reaction system was cooled to room temperature and added with water, the mixture was extracted with ethyl acetate, and the organic phase was dried and evaporated in vacuum to obtain 0.39 g of the product (76%) by column chromatography.

¹HNMR (400 MHz, d₆-DMSO), δ 7.88 (s, 1H), 7.31 (s, 1H), 7.20 (d, 1H), 6.92 (d, 1 H), 5.91(m, 1H), 4.24(dd,2H), 1.26(t,3H)

MS (MM-ES+APCI), m/z: 290 (M+H⁺)

Step 3: 6-(methyl-D3)-2-(trifluoromethyl-2H-chromence-3-carboxylic acid

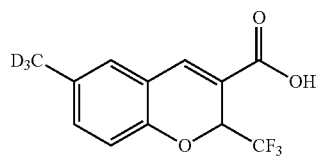

The resulting product (0.3 g, 1.0 mmol) from step 2 was dissolved into a solution (20 mL, alcohol/water=10/1), then slowly added with NaOH (0.12 g, 3.0 mmol), and stirred at room temperature overnight. At the end of reaction, t the reaction system was evaporated to remove alcohol, adjusted pH to 3 and extracted with ethyl acetate/water, and the organic phase was dried and evaporated in vacuum to obtain 0.14 g of the product (54%).

¹HNMR (400 MHz, d₆-DMSO), δ 7.80 (s, 1H), 7.28 (s, 1H), 7.18 (d, 1H), 6.91 (d, 1H), 5.83(m, 1H)

MS (MM-ES+APCI), m/z: 260 (M–H⁺)

Embodiment 2

8-(ethyl-D5)-6-(trifluoromethoxy)-2-(trifluormethyl)-2H-Chromene-3-carboxylic acid

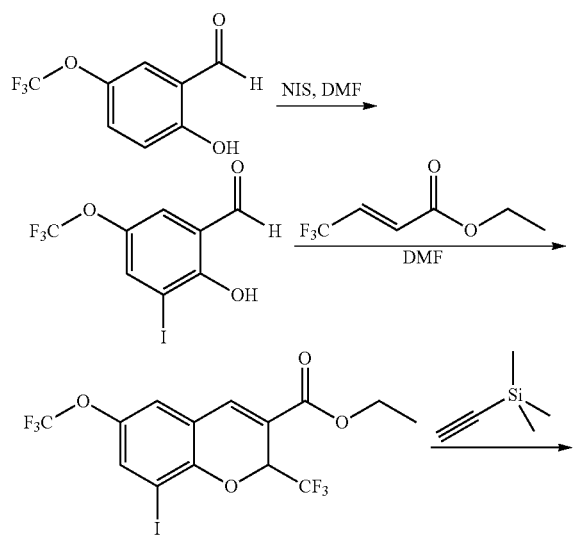

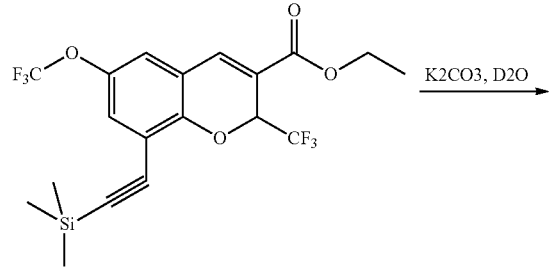

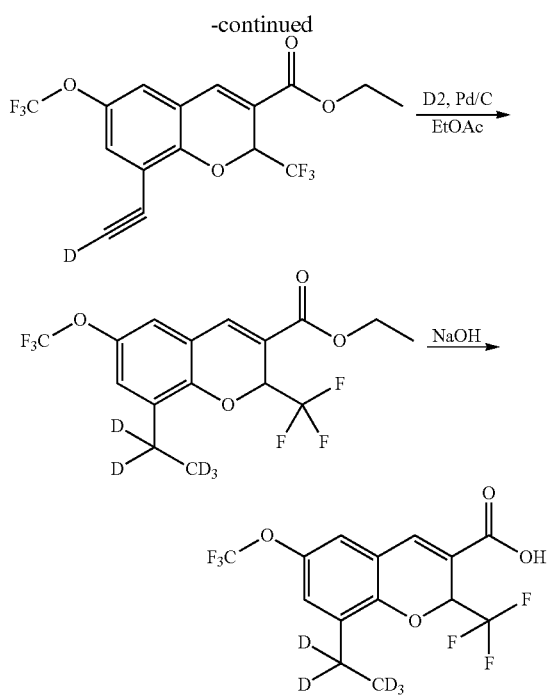

Step 1: 2-hydroxy-3-iodo-5-(trifluoromethoxy) benzaldehyde

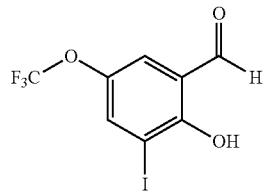 [SMILES: O=Cc1cc(OC(F)(F)F)cc(I)c1O]

2-hydroxy-5-(trifluoromethoxy) benzaldehyde (2.0 g, 9.7 mmol) was dissolved into DMF (20 mL) and then added with NIS (5.4 g, 24 mmol) in batches. The mixture was stirred for 2 days at room temperature. At the end of reaction, saturated sodium thiosulfate solution was added and extracted with ethyl acetate, and the organic phase was dried and evaporated in vacuum to obtain the product (0.30 g, 78%) by column chromatography.

¹HNMR (400 MHz, d-CDCl₃), δ 11.75 (s, 1H), 9.71 (s, 1H), 7.84 (d, 1H), 7.42 (s, 1H)

MS (MM-ES+APCI), m/z: 331 (M–H⁺)

Step 2: ethyl 8-iodo-6-(trifluoromethoxy)-2-(trifluoromethyl)-2H-chromene-3-carboxylate

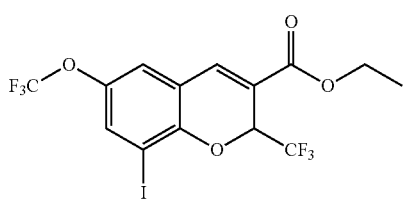 [SMILES: CCOC(=O)C1=Cc2cc(OC(F)(F)F)cc(I)c2OC1C(F)(F)F]

The resulting product (2.5 g, 7.5 mmol) from step 1, triethylamine (2 mL) and ethyl 4,4,4-trifluorocrotonate (5.1 g, 30 mmol) were mixed in DMF (10 mL), and then the system was heated to 85° C. for reaction for 48 hrs. At the end of reaction, the reaction system was cooled to room temperature, added with water and extracted with ethyl acetate, and the organic phase was dried and evaporated in vacuum to obtain 2.5 g of the product (69%) by column chromatography.

$^1$HNMR (400 MHz, d-CDCl$_3$), δ 7.60 (s, 2H), 7.10 (s, 1H), 5.81 (m, 1H), 4.30(dd, 2H), 1.33(m,3H)

MS (MM-ES+APCI), m/z: 481 (M−H$^+$)

Step 3: ethyl 6-(trifluoromethoxy-2-(trifluoromethyl)-8-((trimethylsilyl)ethynyl)-2H-chromen-3-carboxylate

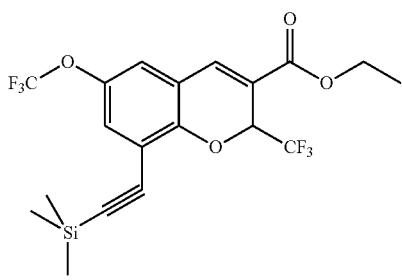 [SMILES: CCOC(=O)C1=Cc2cc(OC(F)(F)F)cc(C#C[Si](C)(C)C)c2OC1C(F)(F)F]

The resulting product (2.5 g, 5.2 mmol) from step 2, CuI (0.29 g, 1.5 mmol), tetra(triphenylphosphine) palladium (0.60 g, 0.50 mmol) and triethylamine (1.2 mL) were mixed in toluene (20 mL), and the system was stirred for 2 days at room temperature under the protection of nitrogen. At the end of reaction, the reaction system was added with water and then extracted with ethyl acetate, and the organic phase was dried and evaporated in vacuum to obtain 2.2 g of the product (94%) by column chromatography.

MS (MM-ES+APCI), m/z: 453 (M+H$^+$)

Step 4: ethyl 8-(ethynyl-D1)-6-(trifluoromethoxy)-2-(trifluoromethyl)-2H-chromene-3-carboxylate

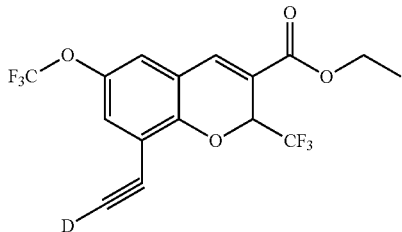 [SMILES: [2H]C#Cc1cc(OC(F)(F)F)cc2c1OC(C(F)(F)F)C(C(=O)OCC)=C2]

The resulting product (2.3 g, 5.0 mmol) from step 3 and K$_2$CO$_3$ (1.4, 10 mmol) were added in alcohol (20 mL), and the system was stirred for 30 min at room temperature and then added with I2O (20 mL). The mixed solution was extracted with ethyl acetate, and the organic phase was dried and evaporated in vacuum to obtain 1.5 g of the product (79%) by column chromatography.

$^1$HNMR (400 MHz, d-CDCl$_3$), δ 7.65 (s, 1H), 7.31 (s, 1H), 7.09 (s, 1H), 5.79 (m, 1H), 4.35(dd,2H), 1.27(t,3H)

MS (MM-ES+APCI), m/z: 382 (M+H$^+$)

Step 5: ethyl 8-(ethyl-D5)-6-(trifluoromethoxy)-2-(trifluoromethyl)-2H-chromene-3-carboxylate

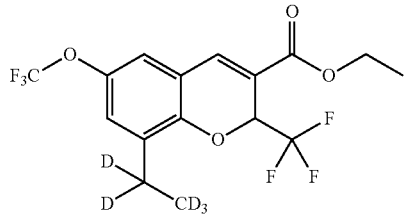 [SMILES: [2H]C([2H])([2H])C([2H])([2H])c1cc(OC(F)(F)F)cc2c1OC(C(F)(F)F)C(C(=O)OCC)=C2]

A sealed bottle was added with the resulting product (0.90 g, 2.4 mmol) from step 4, Pd/C (0.1 g) and ethyl acetate (1.2 mL) and then passed through with O2 for replacement until the sealed bottle was filled up with D$_2$ (30 Psi). The system was reacted for 1 hr at room temperature and then filtered with kieselguhr, and the filtrate was dried and evaporated in vacuum to obtain 0.9 g of the product (96%) by column chromatography.

MS (MM-ES+APCI), m/z: 390 (M+H$^+$)

Step 6: 8-(ethyl-d5)-6-(trifluoromethoxy)-2-(trifluoromethyl)-2H-chromene-3-carboxylic acid

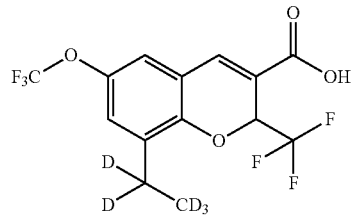 [SMILES: [2H]C([2H])([2H])C([2H])([2H])c1cc(OC(F)(F)F)cc2c1OC(C(F)(F)F)C(C(=O)O)=C2]

The resulting product (0.9 g, 2.3 mmol) from step 5 was dissolved in mixed solution (30 mL, tetrahydrofuran/methanol/water=10/1/1), and the solution was slowly added with NaOH (0.9 g, 24 mmol) and then stirred overnight at room temperature. At the end of reaction, the reaction system was evaporated to remove methanol, then adjusted pH to 3 and extracted with ethyl acetate, and the organic phase was dried and evaporated in vacuum to obtain 0.5 g of the product (62%).

$^1$HNMR (400 MHz, d-CDCl$_3$), δ 7.79 (s, 1H), 7.08 (s, 1H), 6.98 (s, 1H), 5.73(m, 1H)

MS (MM-ES+APCI), m/z: 360 (M−H$^+$)

Embodiment 3

6-chloro-5,7-(dimethyl-D6)-2-(trifluoromethyl)-2H-chromene-3-carboxylic acid

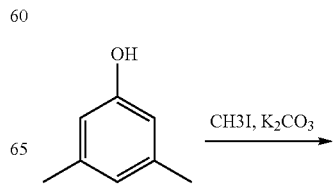

-continued

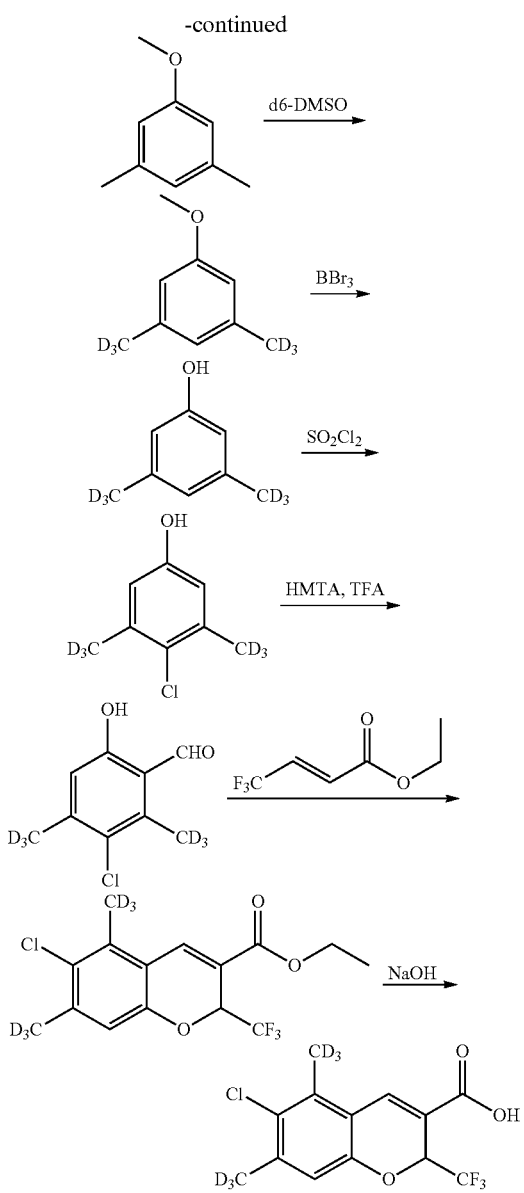

Step 1: 1-methoxy-3, 5-dimethylbenzene

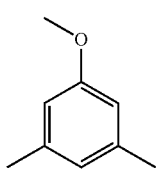

3,5-xylenol (10 g, 0.082 mol) and anhydrous potassium carbonate (34 g, 0.25 mol) were added into DMF (150 mL) and then iodomethane (12.8 g, 0.090 mmol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain 10 g of the product (90%) by column chromatography.

$^1$HNMR (400 MHz, d-CDCl$_3$), δ 6.60(s, 1H), 6.53 (s, 2H), 3.77 (s, 3H), 2.29 (s, 6H)

Step 2: 1-methoxy-3,5-(dimethyl-D6)-benzene

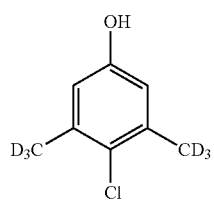

The resulting product (6.0 g, 0.044 mol) from step 1, potassium tert-butoxide (20 g, 0.18 mol) and deuterated DMSO (15 mL) were added into a single-neck bottle, and the system was replaced with argon and then reacted at 120□ for 3 hrs. The reaction system was cooled to room temperature, added with a proper amount of deuterium oxide, oscillated and extracted with ethyl acetate. The organic phase was washed with water, dried and evaporated in vacuum. The obtained liquid was treated again and the post-treatment operations were repeated to obtain 5 g of the product (80%).

$^1$HNMR (400 MHz, d$_6$-DMSO), δ 6.56(s, 1H), 6.53 (s, 1H), 3.7(s, 3H)

Step 3: 3,5-(dimethyl-D6)-phenol

The resulting product (5 g, 0.035 mol) from step 2 was dissolved in anhydrous dichloromethane (20 mL) and then dropwise added with dichloromethane solution (20 mL) of boron tribromide (17.6 g, 0.070 mol) under an ice bath, after dropping, the system continued to be stirred for 2 hrs. At the end of reaction, the reaction system was poured into ice water and then extracted with ethyl acetate, and the organic phase was washed with saturated brine, dried and evaporated in vacuum to obtain 4 g of the product (89%) by column chromatography.

$^1$HNMR (400 MHz, d$_6$-DMSO), δ 9.06(s, 1H), 6.40 (s, 1H), 6.36(s, 1H)

Step 4: 4-chloro-3,5-(dimethyl-D6)-phenol

The resulting product (1.2 g, 9.4 mmol) from step 3 and SO₂Cl₂ (1.27, 9.4 mmol) were added in CCl₄ (20 mL), and the system was refluxed for 5 hrs and then evaporated in vacuum to obtain 1 g of the product (65%) by column chromatography.

¹HNMR (400 MHz, d₆-DMSO), δ 9.37(s, 1H), 6.57 (s, 2H)

Step 5:
3-chloro-6-hydroxy-2,4-(dimethyl-D6)-benzaldehyde

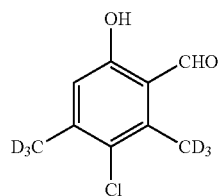 [SMILES: [2H]C([2H])([2H])c1cc(O)c(C=O)c(C([2H])([2H])[2H])c1Cl]

The resulting product (1.0 g, 6.2 mmol) from step 4 was dissolved in trifluoroacetic acid (10 mL), and the system was stirred for 1 hr at 80° C. and then slowly added with hexamethylenetetramine (1 g, 7.1 mmol). The system was reacted at 80° C. for 1 hr, cooled to room temperature, added with 10 mL of water and then stirred for 0.5 hrs. At the end of reaction, saturated sodium bicarbonate solution was added and extracted with ethyl acetate, and the organic phase was washed with brine, dried and evaporated in vacuum to obtain 0.50 g of the product (42%) by column chromatography.

¹HNMR (400 MHz, d₆-DMSO), δ 11.39(s, 1H), 10.36 (s, 1 H), 6.86 (s, 1 H)

Step 6: ethyl 6-chloro-5,7-(dimethyl-D6)-2-(trifluoromethyl)-2H-chromene-3-carboxylate

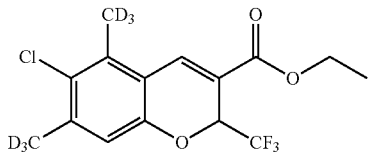 [SMILES: [2H]C([2H])([2H])c1cc2c(c(C([2H])([2H])[2H])c1Cl)C=C(C(=O)OCC)C(C(F)(F)F)O2]

The resulting product (0.50, 2.6 mmol) from step 5, ethyl 4,4,4-trifluorocrotonate (1.7 g, 10.1 mmol) and anhydrous potassium carbonate (0.36 g, 5.6 mmol) were dissolved in DMF (20 mL), and then the system was stirred for 2 hrs at 90° C. At the end of reaction, the reaction system was cooled to room temperature and added with water, the mixture was extracted with ethyl acetate, and the organic phase was dried and evaporated in vacuum to obtain 0.60 g of the product (67%) by column chromatography.

¹HNMR (400 MHz, d₆-DMSO), δ 7.98(s, 1H), 7.01 (s, 1H), 6.0 (m, 1H), 4.28 (dd, 2H), 1.27 (t, 3H)

MS (MM-ES+APCI), m/z: 342(M+H⁺)

Step 7: ethyl 6-chloro-5,7-(dimethyl-D6)-2-(trifluoromethyl)-2H-chromene-3-carboxylic acid

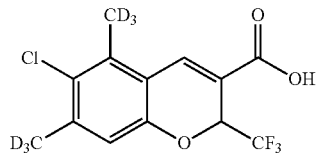 [SMILES: [2H]C([2H])([2H])c1cc2c(c(C([2H])([2H])[2H])c1Cl)C=C(C(=O)O)C(C(F)(F)F)O2]

The resulting product (0.60 g, 1.76 mol) from step 6, sodium hydroxide (704 mg, 17.6 mmol), alcohol (20 mL) and water (2 mL) were added into a single-neck bottle, and the system was stirred overnight at room temperature. At the end of reaction, the reaction system was evaporated to remove alcohol, then adjusted pH to 3 and extracted with ethyl acetate. The organic phase was washed with saturated brine, dried and evaporated in vacuum to obtain 0.50 g of the product (91%).

¹HNMR (400 MHz, d-CDCl₃), δ 8.09(s, 1H), 6.81 (s, 1H), 5.63 (m, 1H)

MS (MM-ES+APCI), m/z: 312(M-H⁺)

Embodiment 4

6-bromo-5,7-(dimethyl-D6)-2-(trifluormethyl)-2H-chromene-3-carboxylic acid

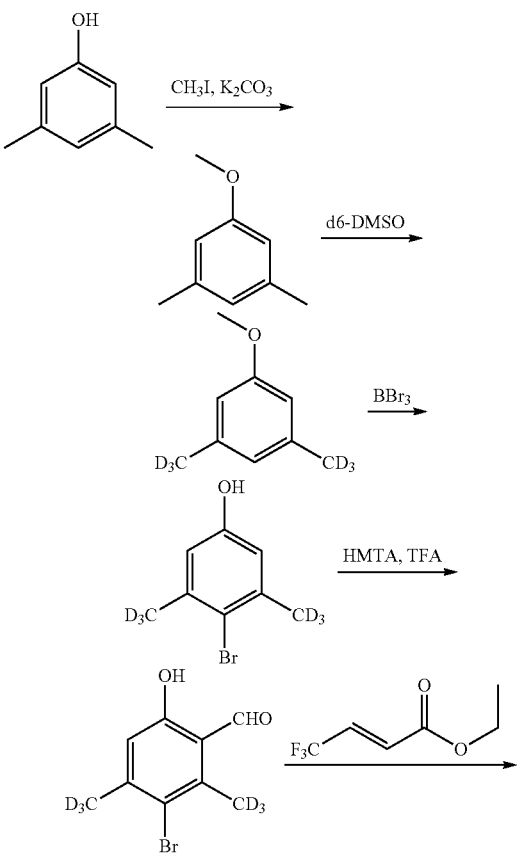

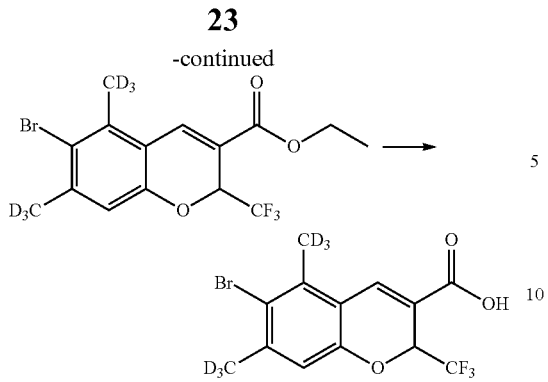

Step 3: 4-bromo-3,5-(dimethyl-D6)-phenol

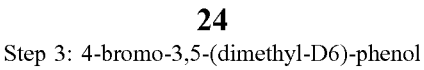

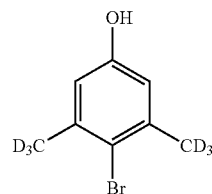

Step 1: 1-methoxy-3, 5-dimethylbenzene

Under the anhydrous conditions, in a single-neck bottle, the resulting product (1.0 g, 8.0 mol) from step 2 was dissolved in dichloromethane (10 mL) and then dropwise added with dichloromethane solution (10 mL) of boron tribromide (4.0 g, 16 mmol) under an ice bath, after dropping, the system continued to be stirred for 2 hrs. At the end of reaction, the reaction system was poured into ice water and then extracted with ethyl acetate, and the organic phase was washed with saturated brine, dried and evaporated in vacuum to obtain 1.3 g of the product (80%) by column chromatography.

$^1$HNMR (400 MHz, d$_6$-DMSO), δ 9.06(s, 1H), 6.39 (s, 1 H), 6.36 (s, 1H)

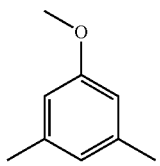

3,5-xylenol (10 g, 0.082 mol) and anhydrous potassium carbonate (34 g, 0.25 mol) were added into DMF (150 mL) and then iodomethane (12.8 g, 0.090 mmol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain 10 g of the product (90%) by column chromatography.

$^1$HNMR (400 MHz, d-CDCl$_3$), δ 6.60(s, 1H), 6.53 (s, 2H), 3.77 (s, 3H), 2.29 (s, 6H)

Step 4: 3-bromo-6-hydroxy-2,4-(dimethyl-D6)-benzaldehyde

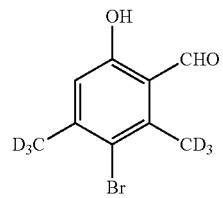

The resulting product (0.50 g, 2.4 mmol) from step 3 was dissolved in trifluoroacetic acid (5 mL) and then slowly added with hexamethylenetetramine (0.41 g, 2.9 mmol). The system was reacted at 80° C. for 1 hr, cooled to room temperature, added with 10 mL of water and then stirred for 0.5 hrs. At the end of reaction, saturated sodium bicarbonate solution was added and extracted with ethyl acetate, and the organic phase was washed with brine, dried and evaporated in vacuum to obtain 0.45 g of the product (79%) by column chromatography.

$^1$HNMR (400 MHz, d$_6$-DMSO), δ 11.9(s, 1H), 10.03 (s, 1H), 7.77(s, 1H), 7.69(s, 1H)

Step 2: 1-methoxy-3,5-(dimethyl-D6)-benzene

Step 5: ethyl 6-bromo-5,7-(dimethyl-D6)-2-(trifluoromethyl)-2H-chromene-3-carboxylate

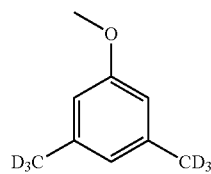

The resulting product (6.0 g, 0.044 mol) from step 1, potassium tert-butoxide (20 g, 0.18 mol) and deuterated DMSO (15 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with water, dried and evaporated in vacuum. The obtained liquid was treated again and the post-treatment operations were repeated to obtain 5 g of the product (80%).

$^1$HNMR (400 MHz, d$_6$-DMSO), δ 6.56(s, 1H), 6.53 (s, 1H), 3.7(s,3H)

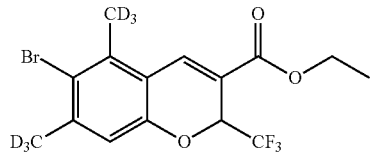 [SMILES: [2H]C([2H])([2H])c1cc2c(c(C([2H])([2H])[2H])c1Br)C=C(C(=O)OCC)C(C(F)(F)F)O2]

The resulting product (0.45 g, 1.9 mmol) from step 4, ethyl 4,4,4-trifluorocrotonate (1.3 g, 7.6 mmol) and anhydrous potassium carbonate (2.6 g, 1.9 mmol) were dissolved in DMF (10 mL), and then the system was stirred for 2 hrs at 90° C. At the end of reaction, the reaction system was cooled to room temperature and added with water, the mixture was extracted with ethyl acetate, and the organic phase was dried and evaporated in vacuum to obtain 0.40 g of the product (55%) by column chromatography.

$^1$HNMR (400 MHz, d-CDCl$_3$), δ 7.88(s, 1H), 6.76 (s, 1H), 5.7(m, 1H), 4.3(dd, 2H), 1.35(t, 3H)

MS (MM-ES+APCI), m/z: 384 (M–H$^+$)

Step 6: ethyl 6-bromo-5,7-(dimethyl-D6)-2-(trifluoromethyl)-2H-chromene-3-carboxylic acid

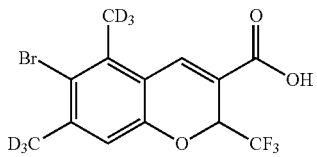 [SMILES: [2H]C([2H])([2H])c1cc2c(c(C([2H])([2H])[2H])c1Br)C=C(C(=O)O)C(C(F)(F)F)O2]

The resulting product (0.4 g, 1.3 mol) from step 5, sodium hydroxide (0.52 g, 13 mol), alcohol (20 mL) and water (2 mL) were added into a single-neck bottle in turn, and the system was stirred overnight at room temperature. At the end of reaction, the reaction system was adjusted with 7% of hydrochloric acid until pH to 7, and extracted with ethyl acetate. The organic phase was washed with saturated brine, dried and evaporated in vacuum to obtain 0.30 g of the product (84%).

$^1$HNMR (400 MHz, d-CDCl$_3$), δ 8.01(s, 1H), 6.78 (s, 1H), 5.77(m, 1H)

MS (MM-ES+APCI), m/z: 356 (M–H$^+$)

Embodiment 5

6-chloro-8-(methyl-D3)-2-(trifluoromethyl)-2H-chromene-3-carboxylic acid

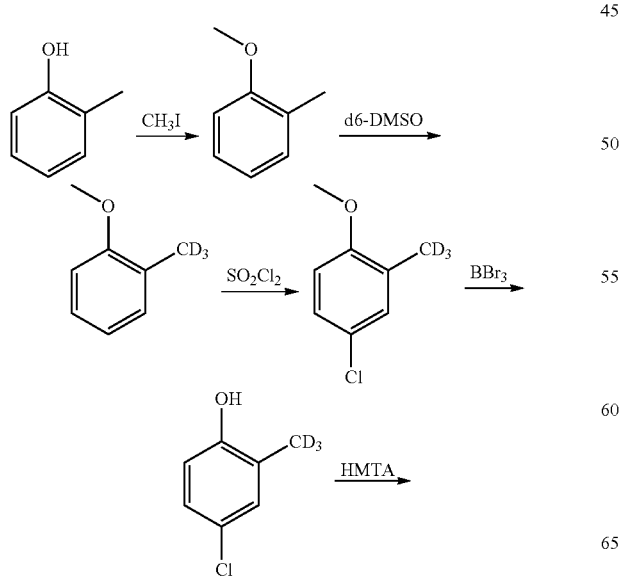

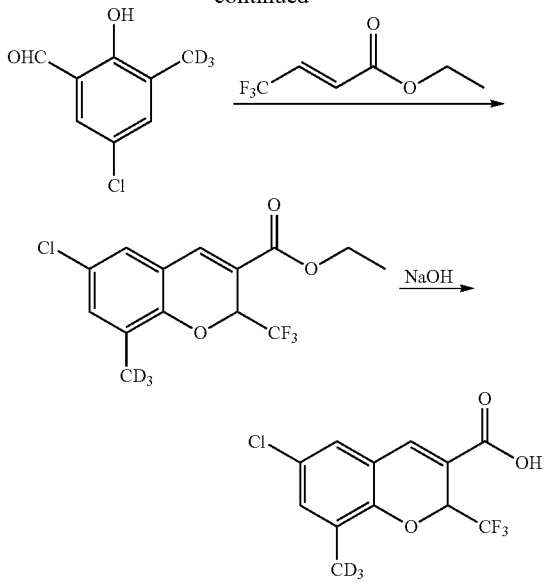

Step 1: 1-methoxy-2-methylbenzene

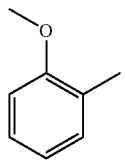

o-cresol (3.0 g, 0.028 mol) and anhydrous potassium carbonate (7.7 g, 0.056 mol) were dissolved into 50 ml of DMF and then iodomethane (3.9 g, 0.028 mmol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain 3 g of the product (89%) by column chromatography.

$^1$HNMR (400 MHz, d$_6$-DMSO), δ 7.15(m, 2H), 6.92 (d, 1H), 6.84 (m, 1H), 3.77 (s, 3H), 2.10(s,3H)

Step 2: 1-methoxy-2-(methyl-D3)-benzene

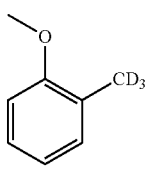

The resulting product (3 g, 0.024 mol) from step 1, potassium tert-butoxide (10.8 g, 0.096 mol) and deuterated DMSO (15 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with water, dried and evaporated in vacuum to obtain 1 g of the product (33%).

$^1$HNMR (400 MHz, d$_6$-DMSO), δ 7.15(m, 2H), 6.92 (d, 1H), 6.84 (m, 1H), 3.77 (s, 3H)

Step 3: 4-chloro-1-methoxy-2-(methyl-D3)-benzene

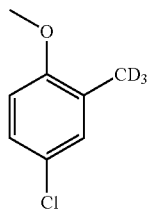

The resulting product (1.0 g, 8 mmol) from step 2 and SO$_2$Cl$_2$ (2.16 g, 16 mmol) were mixed in CCl$_4$ (30 mL), and the system is refluxed for 5 hr and evaporated in vacuum to obtain 1 g of the product (78%) by column chromatography.

$^1$HNMR (400 MHz, d-CDCl$_3$), δ 7.09(d, 2H), 6.80 (d, 1H), 3.80(s, 3H)

Step 4: 4-chloro-2-(methyl-D3)-phenol

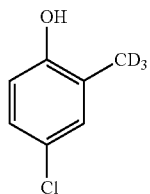 [SMILES: [2H]C([2H])([2H])c1cc(Cl)ccc1O]

Under the anhydrous conditions, in a single-neck bottle, the resulting product (1.0 g, 6.3 mol) from step 3 was dissolved in dichloromethane (10 mL) and then dropwise added with dichloromethane solution (10 mL) of boron tribromide (1.6 g, 12.6 mmol) under an ice bath, after dropping, the system continued to be stirred for 4 hrs. At the end of reaction, the reaction system was poured into ice water and then extracted with dichloromethane, and the organic phase was washed with saturated brine, dried and evaporated in vacuum to obtain 0.8 g of the product (87%) by column chromatography.

$^1$HNMR (400 MHz, d-CDCl$_3$), δ 7.11(s, 1H), 7.06(d, 1H), 6.70(d,1H)

Step 5: 5-chloro-2-hydroxy-3-(methyl-D3)-benzaldehyde

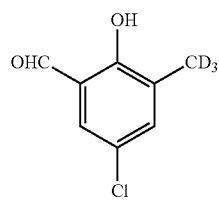 [SMILES: [2H]C([2H])([2H])c1cc(Cl)cc(C=O)c1O]

The resulting product (0.80 g, 5.5 mmol) from step 4 was dissolved in trifluoroacetic acid (5 mL) and then slowly added with hexamethylenetetramine (0.92 g, 6.6 mmol). The system was reacted at 80° C. for 1 hr, cooled to room temperature, added with 10 mL of water and stirred for 0.5 hrs. At the end of reaction, saturated sodium bicarbonate solution was added and extracted with ethyl acetate, and the organic phase was washed with brine, dried and evaporated in vacuum to obtain 0.55 g of the product (57%) by column chromatography.

$^1$HNMR (400 MHz, d-CDCl$_3$), δ 11.18(s, 1H), 9.84 (s, 1 H), 7.55(d, 2H)

Step 6: ethyl 6-chloro-8-(methyl-D3)-2-(trifluoromethyl)-2H-chromene-3-carboxylate

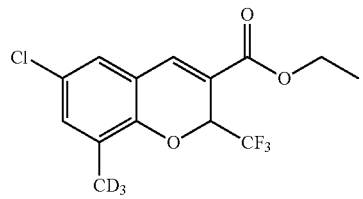

The resulting product (0.50, 2.6 mmol) from step 5, ethyl 4,4,4-trifluorocrotonate (1.7 g, 10.1 mmol) and anhydrous potassium carbonate (0.36 g, 5.6 mmol) were dissolved in DMF (20 mL), and then the system was stirred for 2 hrs at 90° C. At the end of reaction, the reaction system was cooled to room temperature and added with water, the mixture was extracted with ethyl acetate, and the organic phase was dried and evaporated in vacuum to obtain 0.50 g of the product (50%) by column chromatography.

$^1$HNMR (400 MHz, d-CDCl$_3$), δ 7.65(s, 1H), 7.16 (s, 1H), 7.07(s, 1H), 5.73(m, 1H), 4.30(m, 2H), 1.27(m,3H)

Step 7: 6-chloro-8-(methyl-D3)-2-(trifluoromethyl)-2H-chromene-3-carboxylic acid

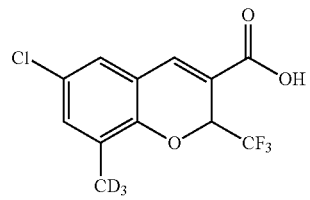 [SMILES: [2H]C([2H])([2H])c1cc(Cl)cc2c1OC(C(F)(F)F)C(C(=O)O)=C2]

The resulting product (0.50 g, 1.54 mol) from step 6, sodium hydroxide (624 mg, 15.6 mmol), alcohol (20 mL) and water (2 mL) were added in a single-neck bottle, and the system was stirred overnight at room temperature. At the end of reaction, the reaction system was evaporated to remove alcohol, then adjusted pH to 3 and extracted with ethyl acetate. The organic phase was washed with saturated brine, dried and evaporated in vacuum to obtain 0.40 g of the product (88%).

¹HNMR (400 MHz, d₆-DMSO), δ 13.4(s, 1H), 7.84 (s, 1H), 7.46(s, 1H), 7.35(s, 1H), 5.96(m, 1H)

Embodiment 6

6-bromo-8-(methyl-D3)-2-(trifluoromethyl)-2H-chromene-3-carboxylic acid

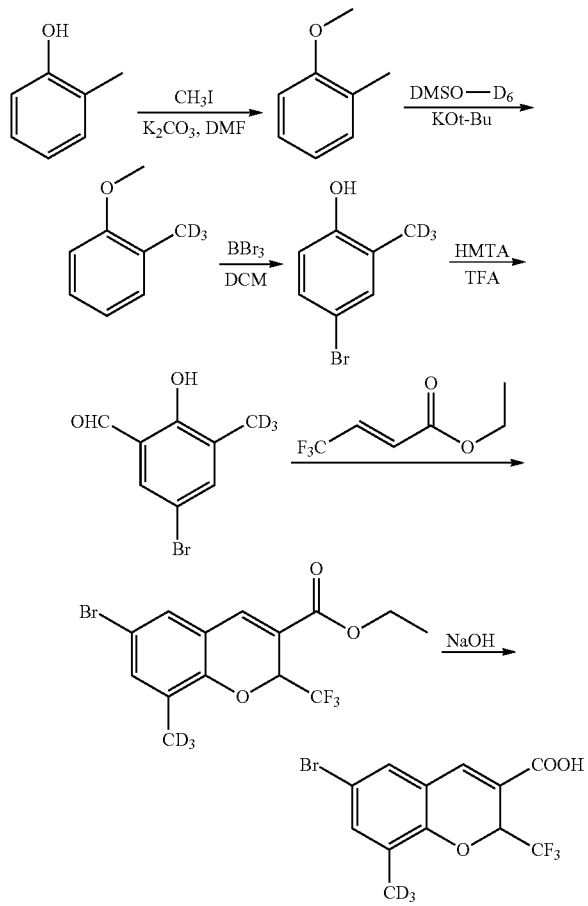

Step 1: 1-methoxy-2-methylbenzene

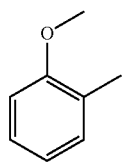

o-cresol (5 g, 0.046 mol) and anhydrous potassium carbonate (19.17 g, 0.14 mol) were dissolved into DMF (75 mL) and then iodomethane (6.65 g, 0.048 mmol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain the product 4.72 g (83.5%) by column chromatography.

MS (MM-ES+APCI), m/z: 123 (M⁺+H⁺)

Step 2: 1-methoxy-2-(methyl-D3)-benzene

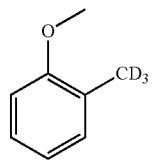

The resulting product (1 g, 8.02 mmol) from step 1, potassium tert-butoxide 3.68 g (33.0 mmol) and deuterated DMSO (2.5 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with brine, dried and evaporated in vacuum. The obtained liquid was treated again and the post-treatment operations were repeated to obtain the product 0.85 g (83%).

¹HNMR (400 MHz, d₆-DMSO), δppm 7.15 (m, 2H), 6.92 (d, 1H, J=0.4 Hz), 6.84 (d, 1H, J=22.4 Hz), 3.77 (s,3H)

Step 3: 4-bromo-2-(methyl-D3)-phenol

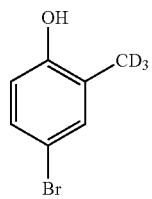 [SMILES: [2H]C([2H])([2H])c1cc(Br)ccc1O]

The resulting product (0.85 g, 6.8 mmol) from step 2 was dissolved in anhydrous dichloromethane (20 mL) and then dropwise added with dichloromethane solution (25 mL) of boron tribromide (1.6 g, 12.6 mmol) under an ice bath, and the system was stirred for 2 hrs at room temperature. At the end of reaction, the reaction system was poured into ice water and then extracted with dichloromethane, and the organic phase was washed with saturated brine, dried and evaporated in vacuum to obtain the product 0.68 g (53%) by column chromatography.

¹HNMR (400 MHz; d-CDCl₃), δppm 7.24(s, 1H), 7.17(d, 1H,J=10.8 Hz), 6.65(d, 1H,J=8.4 Hz)

Step 4: 5-bromo-2-hydroxy-3-(methyl-D3)-benzaldehyde

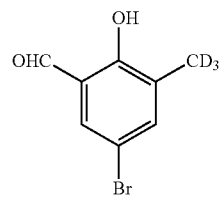 [SMILES: [2H]C([2H])([2H])c1cc(Br)cc(C=O)c1O]

The resulting product (0.68 g, 3.6 mmol) from step 3 was dissolved in trifluoroacetic acid (5 mL), and the system was stirred for 1 hr at 80° C. and then slowly added with hexamethylenetetramine (0.61 g, 4.3 mmol). The system was reacted at 80° C. for 1 hr, cooled to room temperature, added with 10 mL of water and stirred for 0.5 hrs. At the end of reaction, saturated sodium bicarbonate solution was added and extracted with ethyl acetate, and the organic phase was washed with brine, dried and evaporated in vacuum to obtain 0.219 of the product (26.7%) by column chromatography.

¹HNMR (400 MHz, d₆-DMSO), δppm 10.88(s, 1H), 10.03(s, 1H), 7.77(s, 1H), 7.67(s, 1H)

Step 5: ethyl 6-bromo-8-(methyl-D3)-2-(trifluoromethyl)-2H-chromene-3-carboxylate

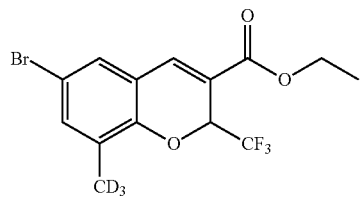 [SMILES: [2H]C([2H])([2H])c1cc(Br)cc2c1OC(C(F)(F)F)C(C(=O)OCC)=C2]

The resulting product (0.21 g, 0.96 mmol) from step 4, ethyl 4,4,4-trifluorocrotonate (0.65 g, 3.80 mmol) and anhydrous potassium carbonate (0.133 g, 0.96 mmol) added in a single-neck bottle were dissolved in DMF (10 mL), and then the system was stirred for 6 hrs at 80° C. The system was added with water and then extracted with ethyl acetate, and the organic phase was dried and evaporated in vacuum to obtain 100 mg of the product (28.2%) by column chromatography.

¹HNMR (400 MHz, d₆-DMSO), δppm 7.91 (s, 1H), 7.63 (s, 1H), 7.49(s, 1H), 6.05(m, 1H), 4.25 (dd,2H,J=6 Hz), 1.27(t,3H)

Step 6: 6-bromo-8-(methyl-D3)-2-(trifluoromethyl)-2H-chromene-carboxylic acid

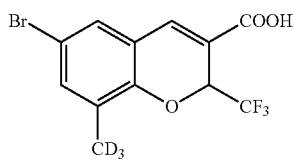

The resulting product (100 mg, 0.27 mol) from step 5, sodium hydroxide (109 mg, 0.27 mmol), alcohol (2 mL) and water (0.2 mL) were added into a single-neck bottle, and the system was stirred overnight at room temperature. At the end of reaction, the reaction system was adjusted pH to 3, and then extracted with ethyl acetate. The organic phase was washed with saturated brine, dried and evaporated in vacuum to obtain 89 mg of the product (96.1%).

¹HNMR (400 MHz, d₆-DMSO), δppm 7.82(s, 1H), 7.56 (s, 1H), 7.46(s, 1H), 5.95(m, 1H)

MS(MM-ES+APCI), m/z: 339 (M–H⁺)

Embodiment 7

6,8-(dimethyl-D6)-2-(trifluoromethyl)-2H-chromene-3-carboxylic acid

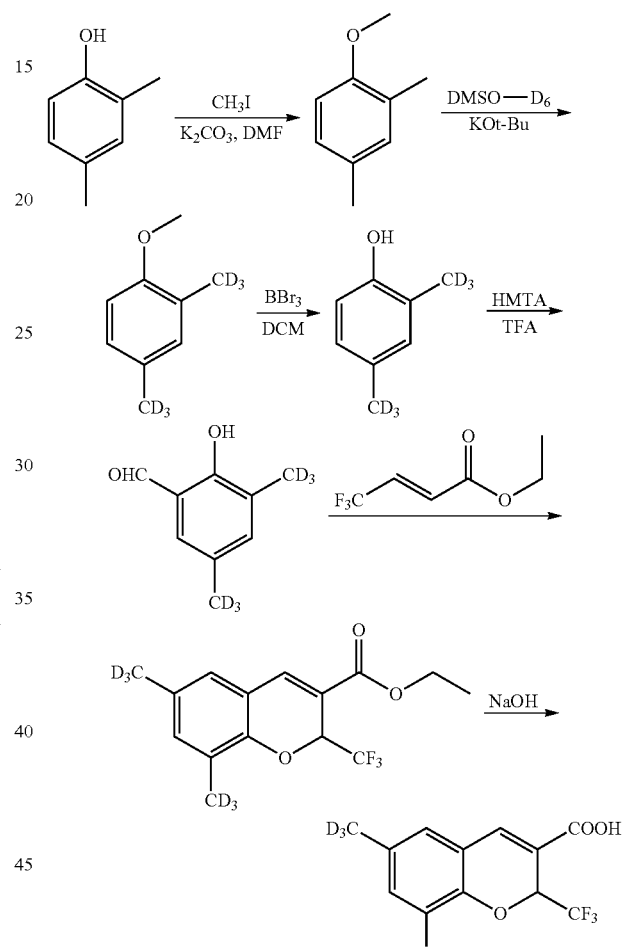

Step 1: 1-methoxy-2,4-dimethylbenzene

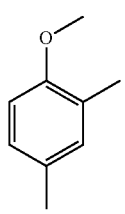

2,4-dimethylphenol (7.5 g, 0.062 mol) and anhydrous potassium carbonate (25.4 g, 0.18 mol) were dissolved into DMF (75 mL) and then iodomethane (8.83 g, 0.062 mol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain 7.11 g of the product (85%) by column chromatography.

MS(MM-ES+APCI), m/z: 137 (M+H$^+$)

Step 2: 1-methoxy-2,4-(dimethyl-D6)-benzene

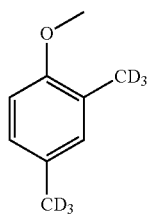

The resulting product (5 g, 0.037 mol) from step 1, potassium tert-butoxide (16.473 g, 0.15 mol) and deuterated DMSO (12 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with water, dried and evaporated in vacuum. The obtained liquid was treated again and the post-treatment operations were repeated to obtain 2.86 g of the product (54.7%).

$^1$HNMR (400 MHz, d$_6$-DMSO), δppm 6.93 (d, 1H, J=2 Hz), 6.90(s, 1H), 6.77(d, 1H), 3.71(s, 3H)

Step 3: 2,4-(dimethyl-D6)-phenol

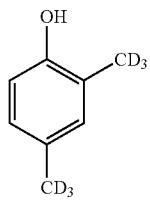

The resulting product (5 g, 0.035 mol) from step 2 was dissolved in anhydrous dichloromethane (80 mL) and then dropwise added with dichloromethane solution (80 mL) of boron tribromide (17.6 g, 0.070 mol) under an ice bath, after dropping, the system continued to be stirred for 4 hrs. At the end of reaction, the reaction system was poured into ice water and then extracted with dichloromethane, and the organic phase was washed with saturated brine, dried and evaporated in vacuum to obtain 3.32 g of the product (73.6%) by column chromatography.

$^1$HNMR(400 MHz, d$_6$-DMSO), δppm 8.87(s, 1H), 6.81(s, 1H), 6.73(d, 1H), 6.60(d, 1H)

Step 4: 2-hydroxy-3,5-(dimethyl-D6)-benzaldehyde

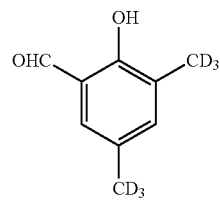 [SMILES: [2H]C([2H])([2H])c1cc(C=O)c(O)c(C([2H])([2H])[2H])c1]

The resulting product (3.32 g, 0.026 mol) from step 3 was dissolved in trifluoroacetic acid (20 mL), and the system was stirred for 1 hr at 80° C. and then slowly added with hexamethylenetetramine (4.37 g, 0.031 mol). The system was reacted at 80° C. for 1 hr, cooled to room temperature, added with 10 mL of water and stirred for 0.5 hrs. At the end of reaction, saturated sodium bicarbonate solution was added and extracted with ethyl acetate, and the organic phase was washed with brine, dried and evaporated in vacuum to obtain 2.04 g of the product (49.6%) by column chromatography.

$^1$HNMR(400 MHz, d$_6$-DMSO), δppm 10.78(s, 1H), 9.98 (s, 1H), 7.37(s, 1H), 7.31(s, 1H)

Step 5: ethyl 6,8-(dimethyl-D6)-2-(trifluoromethyl)-2H-chromene-3-carboxylate

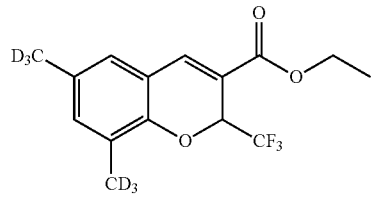

The resulting product (2.02 g, 0.013 mol) from step 4, ethyl 4,4,4-trifluorocrotonate (4.30 g, 0.026 mol) and anhydrous potassium carbonate (1.76 g, 0.013 mol) were dissolved in DMF (70 mL), and then the system was stirred for 6 hrs at 80° C. At the end of reaction, the reaction system was cooled to room temperature, added with water and then extracted with ethyl acetate, and the organic phase was dried and evaporated in vacuum to obtain 2.35 g of the product (60.1%) by column chromatography.

$^1$HNMR(400 MHz, d$_6$-DMSO), δppm 7.84(s, 1H), 7.13(s, 1H), 7.09(s, 1H), 5.94(m, 1H), 4.25(dd, 1H), 1.27 (t,3H)

Step 6: 6,8-(dimethyl-D6)-2-(trifluoromethyl)-2H-chromene-3-carboxylic acid

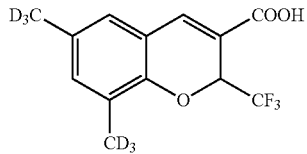 [SMILES: [2H]C([2H])([2H])c1cc2c(c(C([2H])([2H])[2H])c1)OC(C(F)(F)F)C(C(=O)O)=C2]

The resulting product (2.35 g, 7.68 mmol) from step 5, sodium hydroxide (3 g, 76.8 mmol), alcohol (40 mL) and water (4 mL) were added into a single-neck bottle in turn, and the system was stirred overnight at room temperature. At the end of reaction, the reaction system was adjusted pH to 3, and then extracted with ethyl acetate. The organic phase was washed with saturated brine, dried and evaporated in vacuum to obtain 1.61 g of the product (75.4%).

$^1$HNMR(400 MHz, $d_6$-DMSO), δppm 13.19(s, 1H), 7.77 (s, 1H), 7.10(s, 1H), 7.80(s, 1H), 5.88(m, 1H)

MS(MM-ES+APCI), m/z: 277 (M−H$^+$)

Embodiment 8

8-chloro-6-(methyl-D3)-2-(trifluoromethyl)-2H-chromene-3-carboxylic acid

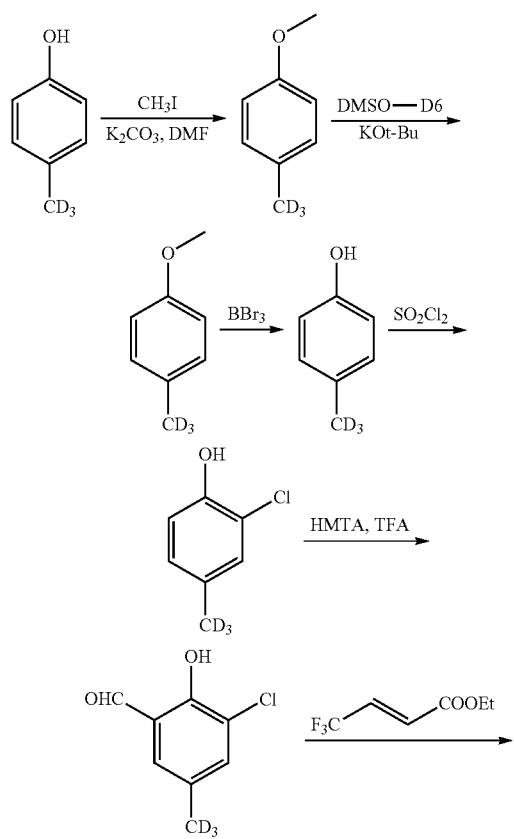

Step 1: 1-methoxy-4-methylbenzene

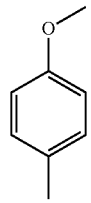

p-cresol (20 g, 0.19 mol) and anhydrous potassium carbonate (75 g, 0.54 mol) were added into DMF (500 mL) and then iodomethane (27 g, 0.19 mol) was dropped under an ice bath. The system was stirred overnight at room temperature. At the end of reaction, the reaction system was added with water and then extracted with ethyl acetate, and the organic phase was washed with saturated brine, then dried and evaporated in vacuum to obtain 20 g of the product (86%) by column chromatography.

MS(MM-ES+APCI), m/z: 123 (M+H$^+$)

Step 2: 1-methoxy-4-(methyl-D3)-benzene

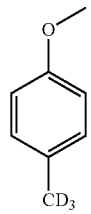

The resulting product (20 g, 0.16 mol) from step 1, potassium tert-butoxide (76 g, 0.64 mol) and deuterated DMSO (60 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with water, dried and evaporated in vacuum. The obtained liquid was treated again and the post-treatment operations were repeated to obtain 10 g of the product (50%).

MS(MM-ES+APCI), m/z: 126 (M+H$^+$)

Step 3: 4-(methyl-D3)-phenol

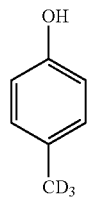

The resulting product (2.0 g, 0.016 mol) from step 2 was dissolved in anhydrous dichloromethane (40 mL) and then dropwise added with dichloromethane solution (40 mL) of boron tribromide (8.0 g, 0.032 mol) under an ice bath, after dropping, the system continued to be stirred for 2 hrs. At the end of reaction, the reaction system was poured into ice water and then extracted with dichloromethane, and the organic phase was washed with saturated brine, dried and evaporated in vacuum to obtain 1 g of the product (58%) by column chromatography.

Step 4: 2-chloro-4-(methyl-D3)-phenol

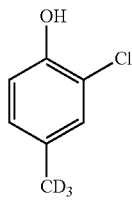

The resulting product (1.0 g, 9.0 mmol) from step 3 and SO$_2$Cl$_2$ (1.2 g, 9.0 mmol) were added in CCl$_4$ (20 mL), and the system was refluxed for 5 hrs and then evaporated in vacuum to obtain 0.60 g of the product (46%) by column chromatography.

Step 5: 3-chloro-2-hydroxy-5-(methyl-D3)-benzaldehyde

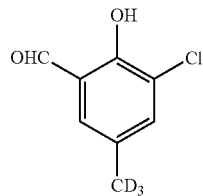 [SMILES: [2H]C([2H])([2H])c1cc(Cl)c(O)c(C=O)c1]

The resulting product (0.60 g, 4.1 mmol) from step 4 was dissolved in trifluoroacetic acid (20 mL), and the system was stirred for 1 hr at 80° C. and then slowly added with hexamethylenetetramine (0.69 g, 4.9 mmol). The system was reacted at 80° C. for 1 hr, cooled to room temperature, added with 10 mL of water and then stirred for 0.5 hrs. At the end of reaction, saturated sodium bicarbonate solution was added and extracted with ethyl acetate, and the organic phase was washed with brine, dried and evaporated in vacuum to obtain 0.25 g of the product (35%) by column chromatography.

$^1$HNMR (400 MHz, d$_6$-DMSO), δ 10.9(s, 1H), 10.11 (s, 1H), 7.60 (s, 1H), 7.52 (s, 1H)

Step 6: ethyl 8-chloro-6-(methyl-D3)-2-(trifluormethyl)-2H-chromene-3-carboxylate

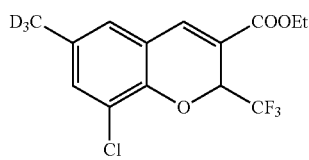 [SMILES: [2H]C([2H])([2H])c1cc(Cl)c2c(c1)C=C(C(=O)OCC)C(C(F)(F)F)O2]

The resulting product (0.25 g, 1.4 mmol) from step 5, ethyl 4,4,4-trifluorocrotonate (0.48 g, 2.8 mmol) and anhydrous potassium carbonate (0.46 g, 2.8 mmol) were dissolved in DMF (10 mL), and then the system was stirred for 3 hrs at 90° C. At the end of reaction, the reaction system was cooled to room temperature and added with water, the mixture was extracted with ethyl acetate, and the organic phase was dried and evaporated in vacuum to obtain 0.2 g of the product (44%) by column chromatography.

$^1$HNMR (400 MHz, d$_6$-DMSO), δ 7.39(s, 1H), 7.31 (s, 1H), 6.1 (m, 1H), 4.27 (dd, 2H), 1.30 (t, 3H)

MS (MM-ES+APCI), m/z: 325 (M+H$^+$)

Step 7: 8-chloro-6-(methyl-D3)-2-(trifluoromethyl)-2H-chromene-3-carboxylic acid

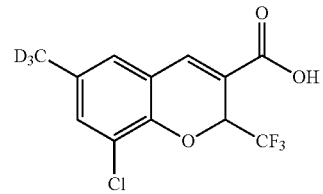 [SMILES: [2H]C([2H])([2H])c1cc(Cl)c2c(c1)C=C(C(=O)O)C(C(F)(F)F)O2]

The resulting product (020 g, 0.60 mmol) from step 6, sodium hydroxide (0.48 g, 12 mmol), alcohol (20 mL) and water (2 mL) were added into a single-neck bottle, and the system was stirred overnight at room temperature. At the end of reaction, the reaction system was adjusted pH to 3 and extracted with ethyl acetate. The organic phase was washed with saturated brine, dried and evaporated in vacuum to obtain 0.15 g of the product (85%).

$^1$HNMR (400 MHz, d-CDCl$_3$), δ 8.09(s, 1H), 6.81 (s, 1H), 5.63 (m, 1H)

MS (MM-ES+APCI), m/z: 395(M–H$^+$)

Embodiment 9

6,8-dibromo-5,7-(dimethyl-D6)-2-(trifluoromethyl)-2H-chromene-3-carboxylic acid

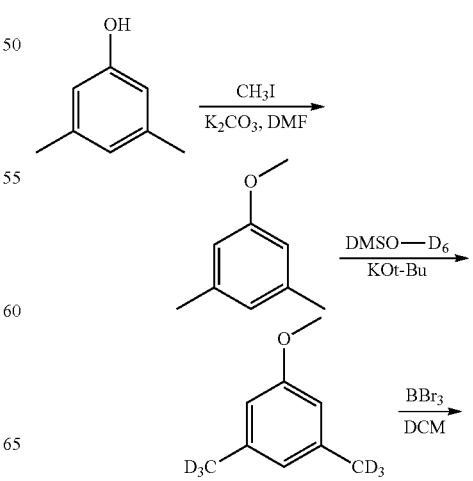

Step 2: 1-methoxy-3,5-(dimethyl-D6)-benzene

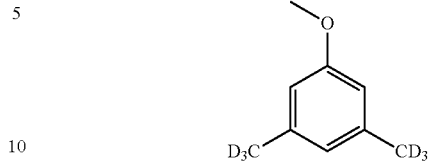

The resulting product (6.0 g, 0.044 mol) from step 1, potassium tert-butoxide (20 g, 0.18 mol) and deuterated DMSO (15 mL) were added into a single-neck bottle, and the system was replaced with argon and then reacted at 120° C. for 3 hrs. The reaction system was cooled to room temperature, added with a proper amount of deuterium oxide, oscillated and extracted with ethyl acetate. The organic phase was washed with water, dried and evaporated in vacuum. The obtained liquid was treated again and the post-treatment operations were repeated to obtain 5 g of the product (80%).

$^1$HNMR (400 MHz, $d_6$-DMSO), δ 6.56(s, 1H), 6.55(s, 1H), 6.53 (s, 1H), 3.7(s, 3H)

Step 3: 4-bromo-3,5-(dimethyl-D6)-phenol

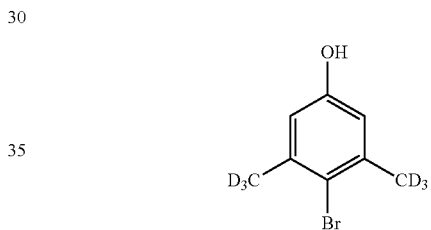

Under the anhydrous conditions, in a single-neck bottle, the resulting product (1.0 g, 8.0 mmol) from step 2 was dissolved in dichloromethane (10 mL) and then dropwise added with dichloromethane solution (10 mL) of boron tribromide (4.0 g, 16 mmol) under an ice bath, after dropping, the system continued to be stirred for 2 hrs. At the end of reaction, the reaction system was poured into ice water and then extracted with dichloromethane, and the organic phase was washed with saturated brine, dried and evaporated in vacuum to obtain 1.3 g of the product (80%) by column chromatography.

$^1$HNMR (400 MHz, $d_6$-DMSO), δ 9.92(s, 1H), 6.58(s, 2H).

Step 4: 2,4-dibromo-3,5-(dimethyl-D6)-phenol

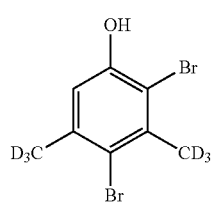 [SMILES: [2H]C([2H])([2H])c1cc(O)c(Br)c(C([2H])([2H])[2H])c1Br]

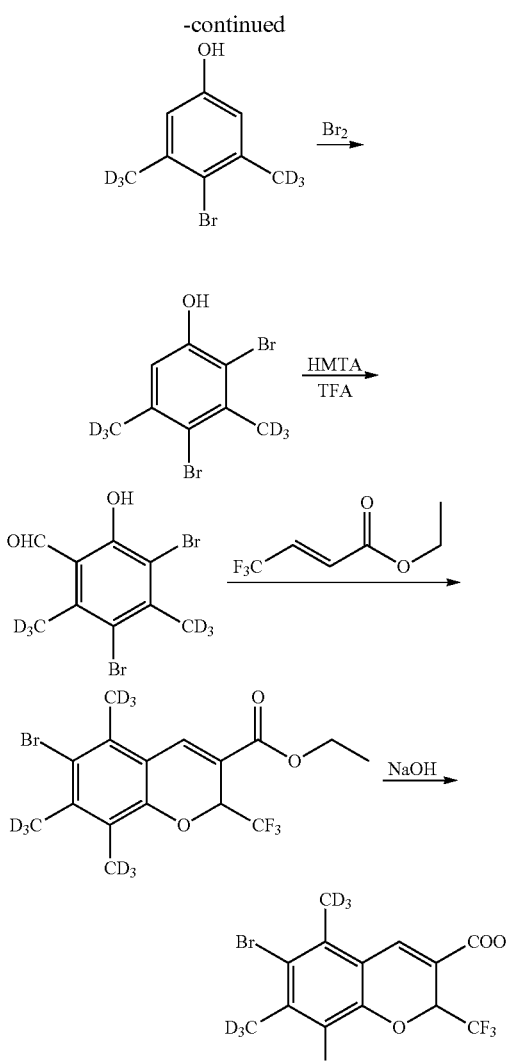

Step 1: 1-methoxy-3, 5-dimethyl-benzene

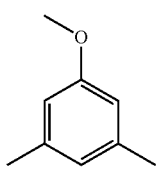

3,5-xylenol (10 g, 0.082 mol) and anhydrous potassium carbonate (34 g, 0.25 mol) were added into DMF (150 mL) and then iodomethane (12.8 g, 0.090 mol) was dropped under an ice bath. The mixture was stirred overnight at room temperature. At the end of reaction, the reaction system was added with water and then extracted with ethyl acetate, and the organic phase was washed with saturated brine, then dried and evaporated in vacuum to obtain 10 g of the product (90%) by column chromatography.

1HNMR (400 MHz, d-CDCl$_3$), δ 6.60(s, 1H), 6.53 (s, 2H), 3.77(s, 3H), 2.29 (s, 6H)

Under the anhydrous conditions, the resulting product (1 g, 4.83 mmol) from step 3 was dissolved in dichlormethane (10 mL) and then dropwise added with dichloromethane solution (5 mL) of liquid bromine (0.81 g, 5.07 mmol) under an ice bath, after dropping, the system continued to be stirred overnight at room temperature. At the end of reaction, the reaction system was added with sodium hydrogen sulfite solution for removing excessive bromine, evaporated to remove dichloromethane and extracted with ethyl acetate/water. The organic phase was washed with saturated brine, dried and evaporated in vacuum to obtain 1.25 g of the product (90.5%) by column chromatography.

$^1$HNMR (400 MHz, d$_6$-DMSO), δ 10.30(s, 1H), 6.82 (s, 1H)

Step 5: 3,5-dibromo-2-hydroxy-4,6-(dimethyl-D6)-benzaldehyde

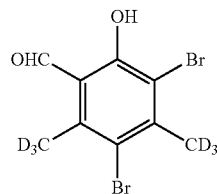 [SMILES: [2H]C([2H])([2H])c1c(Br)c(O)c(C=O)c(C([2H])([2H])[2H])c1Br]

The resulting product (0.50 g, 1.75 mmol) from step 4 was dissolved in trifluoroacetic acid (5 mL), and the mixture was slowly added with hexamethylenetetramine (0.29 g, 2.10 mmol). The system was reacted at 80° C. for 1 hr, cooled to room temperature, added with 10 mL of water and then stirred for 0.5 hrs. At the end of reaction, saturated sodium bicarbonate solution was added and extracted with ethyl acetate, and the organic phase was washed with brine, dried and evaporated in vacuum to obtain 0.34 g of the product (61.9%) by column chromatography.

$^1$HNMR (400 MHz, d$_6$-DMSO), δ 12.72(s, 1H), 10.30 (s, 1H)

Step 6: ethyl 6,8-dibromo-5,7-(dimethyl-D6)-2-(trifluormethyl)-2H-chromene-3-carboxylate

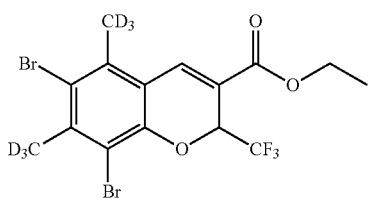 [SMILES: [2H]C([2H])([2H])c1c(Br)c2c(c(C([2H])([2H])[2H])c1Br)C=C(C(=O)OCC)C(C(F)(F)F)O2]

The resulting product (0.34 g, 1.08 mmol) from step 5, ethyl 4,4,4-trifluorocrotonate (0.72 g, 4.32 mmol) and anhydrous potassium carbonate (0.15 g, 1.08 mmol) were dissolved in DMF (6 mL), and then the system was stirred for 6 hrs at 90° C. At the end of reaction, the reaction system was cooled to room temperature and added with water, the mixture was extracted with ethyl acetate, and the organic phase was dried and evaporated in vacuum to obtain 0.12 g of the product (23.9%) by column chromatography.

1HNMR (400 MHz, d-CDCl$_3$), δ 7.95(s, 1H), 5.80(m, 1H), 4.34(dd, 2H), 1.36(t, 3H)

Step 7: 6,8-dibromo-5,7-(dimethyl-D6)-2-(trifluoromethyl)-2H-chromene-3-carboxylic acid

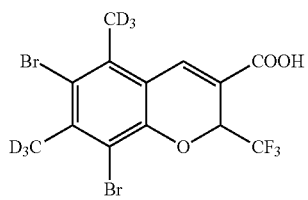 [SMILES: [2H]C([2H])([2H])c1c(Br)c2c(c(C([2H])([2H])[2H])c1Br)C=C(C(=O)O)C(C(F)(F)F)O2]

The resulting product (0.12 g, 0.26 mmol) from step 6, sodium hydroxide (0.10 g, 2.6 mmol), alcohol (4 mL) and water (0.4 mL) were added into a single-neck bottle, and the system was stirred overnight at room temperature. The reaction system was adjusted with 7% hydrochloric acid until pH to 7 and extracted with ethyl acetate. The organic phase was washed with saturated brine, dried and evaporated in vacuum to obtain 43 mg of the product (38.0%).

$^1$HNMR (400 MHz, d-CDCl$_3$), δ 8.08(s, 1H), 5.77(m, 1H)
MS (MM-ES+APCI), m/z: 435 (M–H$^+$)

Embodiment 10

7-(methyl-D3)-2-(trifluoromethyl)-2H-chromene-3-carboxylic acid

The synthetic method refers to Embodiment 1.
$^1$HNMR (400 MHz, d-CDCl$_3$), δ 7.86(s, 1H), 7.13 (d, 1H), 7.00 (s, 1H), 6.75 (d, 1H), 5.36 (m, 1H)

Embodiment 11

7-(hexyl-D13)-2-(trifluoromethyl)-2H-chromene-3-carboxylic acid

The synthetic method refers to Embodiment 1.
$^1$HNMR (400 MHz, d-CDCl$_3$), δ 7.92(s, 1H), 7.12 (d, 1H), 6.64 (d, 1H), 6.62 (s, 1H), 5.43 (m, 1H)

Embodiment 12

6-chloro-7-(methyl-D3)-2-(trifluoromethyl)-2H-chromene-3-carboxylic acid

The synthetic method refers to Embodiment 1.
$^1$HNMR (400 MHz, d-CDCl$_3$), δ 8.03(s, 1H), 7.06 (s, 1H), 6.50 (s, 1H), 5.46 (m, 1H)

Embodiment 13

8-(1-methylhexyl-D15)-2-trifluoromethyl)-2H-chromene-3-carboxylic acid

The synthetic method refers to Embodiment 1.
$^1$HNMR (400 MHz, d-CDCl$_3$), δ 7.86(s, 1H), 7.46 (d, 1H), 7.27 (d, 1H), 6.75 (m, 1H), 5.43 (m, 1H)

Embodiment 14

6-chloro-8-(methyl-D3)-2-(trifluoromethyl)-2H-chromene-3-carboxylic acid

The synthetic method refers to Embodiment 1.
$^1$HNMR (400 MHz, d-CDCl$_3$), δ 8.01(s, 1H), 6.85 (s, 1H), 6.77 (s, 1H), 5.35 (m, 1H)

Embodiment 15

6-chloro-7-(1,1-dimethylhexyl-D17)-2-(trifluoromethyl)-2H-chromene-3-carboxylic acid The synthetic method refers to Embodiment 1.
$^1$HNMR (400 MHz, d-CDCl$_3$), δ 7.95(s, 1H), 7.10 (s, 1H), 6.73 (s, 1H), 5.51 (m, 1H)

Embodiment 16

6-chlor-8-(1-methylhexyl-D15)-2-(trifluoromethyl)-2H-chromene-3-carboxylic acid

The synthetic method refers to Embodiment 1.
$^1$HNMR (400 MHz, d-CDCl$_3$), δ 7.98 (s, 1H), 7.25 (s, 1H), 6.99 (s, 1H), 5.41 (m, 1H)

Embodiment 17

7-(1-methylhexyl-D15)-2-(trifluoromethyl)-2H-chromene-3-carboxylic acid

The synthetic method refers to Embodiment 1.
$^1$HNMR (400 MHz, d-CDCl$_3$), δ7.92(s, 1H), 7.09 (d, 1H), 6.65 (d, 1H), 5.48 (m, 1H)

Embodiment 18

6-chloro-7-(hexyl-D13)-2-(trifluoromethyl)-2H-chromene-3-carboxylic acid

The synthetic method refers to Embodiment 1.
$^1$HNMR (400 MHz, d-CDCl$_3$), δ 8.05(s, 1H), 7.12 (s, 1H), 7.00 (s, 1H), 5.48 (m, 1H)

Embodiment 19

8-(hexyl-D13)-2-(trifluoromethyl)-2H-chromene-3-carboxylic acid

The synthetic method refers to Embodiment 1.
$^1$HNMR (400 MHz, d-CDCl$_3$), δ 8.09(s, 1H), 7.48(d, 1H), 7.04(d, 1H), 6.78 (m, 1H), 5.54 (m, 1H)

Embodiment 20

7,8-(dimethyl-D6)-2-(trifluoromethyl)-2H-chromene-3-carboxylic acid

The synthetic method refers to Embodiment 1.
$^1$HNMR (400 MHz, d-CDCl$_3$), δ 7.95 (s, 1H), 6.94 (d, 1H), 6.63 (d, 1H), 5.56(m, 1H)

Embodiment 21

6-chloro-8-(hexy-D13)-2-(trifluoromethyl)-2H-chromene-3-carboxylic acid

The synthetic method refers to Embodiment 1.
$^1$HNMR (400 MHz, d-CDCl$_3$), δ 8.05(s, 1H), 7.24(s, 1H), 6.99 (s, 1H), 5.24 (m, 1H)

Embodiment 22

Deuterated benzopyran compounds of different concentrations were uniformly mixed with ovine COX-1 and human recombinant COX-2 for incubation for 15 min, respectively, and then the system was added with Heme and ADHP for incubation for another 2 min and finally added with substrate arachidonic acid. The light emission intensity of the reaction product at 595 nm was immediately detected by a microplate reader under exciting light at 530 nm. The results showed that deuterated benzopyran compounds may significantly inhibit the enzyme reaction rate of COX-2 and have good selectivity. In the whole blood assay, venous blood of healthy donors was collected with a non-anticoagulation tube and a heparin tube, deuterated benzopyran compounds of different concentrations ($1\times10^{-8}$ to $1\times10^{-4}$) were mixed with the blood in the non-anticoagulation tube, the supernatant was collected after the blood was coagulated and then measured by ELISA in terms of the yield of TXB2; and deuterated benzopyran compounds of different concentrations ($1\times10^{-8}$ to $1\times10^{-4}$) were mixed with the blood in the heparin tube, the mixture was added with lipopolysaccharide until the final concentration was 100 μg/mL, mixed uniformly and then kept stand overnight at 37° C., the supernatant was collected by centrifugation and then measured by ELISA in terms of the yield of PGE2. According to the inhibition effects of the deuterated benzopyran compounds on the two isomerases and the inhibition effects of the deuterated benzopyran compounds on TXB2/PGE2 in the blood, 50% inhibitory concentration (IC50) values are calculated as shown in Table 1. (The used compounds were compounds prepared in Embodiments 1-9 and expressed by Drug No. in Table 1, and GIBH-1006, GIBH-1004, GIBH-1016, GIBH-1008, GIBH-1010, GIBH-1012, GIBH-1014, GIBH-1018 and GIBH-1051 were corresponding to the compounds prepared in Embodiments 1-9, respectively.)

TABLE 1

Inhibition IC50 of part of compounds onto two isomerases COXs and inhibition IC50 onto generation of TXB2/PGE2 in the whole blood test

| Drug No. | COX-1 | COX-2 | TXB2 | PGE2 |
|---|---|---|---|---|
| GIBH-1006 | >100 uM | 56.06 nM | 20.5 uM | 79.5 uM |
| GIBH-1004 | >100 uM | >10 uM | >100 uM | 67.5 uM |
| GIBH-1016 | >100 uM | 179.5 nM | >100 uM | >100 uM |
| GIBH-1008 | >100 uM | 61.75 nM | 65.1 uM | 78.5 uM |
| GIBH-1010 | >100 uM | 67.10 nM | 38.9 uM | >100 uM |
| GIBH-1012 | >100 uM | 54.46 nM | >100 uM | >100 uM |
| GIBH-1014 | 31.75 uM | 36.84 nM | >100 uM | 45.22 uM |
| GIBH-1018 | >100 uM | 63.74 nM | >100 uM | 78.90 uM |
| GIBH-1051 | 5.446 uM | 84.10 nM | 70.64 uM | >100 uM |

It can be seen from the enzyme activity test as shown in Table 1 that, a series of compounds of the present invention have a nanomole level of inhibition IC50 values onto the activity of human recombinant COX-2 and has relatively poor inhibition onto the activity of COX-1. It is indicated that COX-2 has better section inhibition. For example, the IC50 value of the enzyme COX-2 of the compound CIBH1008 is 61.75 nanomole, while the IC50 value of COX-1 is greater than 100 nanomole. Thus, a ratio of the selectivity of the compound CIBH1008 to COX-2 to the selectivity of the compound CIBH1008 to COX-1 is greater than 1619, a ratio of the selectivity of the compound CIBH-1018 to COX-2 to the selectivity of the compound CIBH-1018 to COX-1 is greater than 1569, and a ratio of the selectivity of the compound CIBH-1014 to COX-2 to the selectivity of the compound CIBH-1014 to COX-1 is 862. The human whole blood COX enzyme activity test also indicates that the compounds GIBH1014 and GIBH1018 and the compound CIBH-1014 have better selectivity to the inhibition of COX-2 enzyme of blood cells.

Embodiment 23

Test on pharmacokinetics and bioavailability of rats: four male SD rats per group, single-dose, oral administration 2.5-25 mg/kg, vein 1-5 mg/kg, animal blood samples are collected at proper time points after drug administration, heparin anticoagulation, 3000 rpm*10 min, collect supernatant, storage at −20° C. for LC/MS analysis. The blood samples employ acetonitrile to precipitate protein, 16000 rpm*30 min, and the supernatant is used for LC/MS analysis. Data is performed with parameter fitting by DAS2.0, and the bioavailability of oral administration of compounds is calculated according AUC data. The results refer to the following table.

TABLE 3

Pharmacokinetic study results of part of compounds

| | Rat PK | | | | | | |
|---|---|---|---|---|---|---|---|
| | The number of animals | Dose mg/kg | AUC ug/L*h | Cmax ug/l | t½ h | Tmax h | BA % | Vd l/kg |
| GIBH-1006 | ♂4 | 25 | 511440.9 | 29525 | 9.54 | 1.625 | 78.6 | 0.68 |
| GIBH-1004 | ♂4 | 25 | 180839.6 | 34150 | 2.88 | 0.563 | 46.1 | 0.58 |
| GIBH-1016 | ♂4 | 2.5 | 4325.4 | 4405 | 1.04 | 0.187 | 65.1 | 0.94 |
| GIBH-1008 | ♂4 | 10 | 118331.4 | 20900 | 2.1 | 1.167 | 92.8 | 0.26 |
| GIBH-1010 | ♂4 | 10 | 84789.7 | 21399 | 3.35 | 0.5 | 111.8 | 0.57 |
| GIBH-1012 | ♂4 | 2.5 | 38881.9 | 8945 | 3.37 | 0.5 | 110.7 | |
| GIBH-1014 | ♂4 | 10 | 142687 | 35300 | 5.2 | 0.417 | 107.4 | 0.53 |
| GIBH-1018 | ♂4 | 2.5 | 28340.5 | 11805 | 2.43 | 0.271 | 90.6 | 0.31 |
| GIBH-1051 | ♂4 | 2.5 | 13028.2 | 4485 | 1.759 | 0.688 | 63.7 | 1.004 |

AUC (Area Under the Curve): the area under the curve of concentration of drug in blood plasma against time, standing for the bioavailability of drug (the fraction of drug absorbed by human body). The larger the AUC is, the higher the bioavailability is; otherwise, the bioavailability is low. The AUC is called "area under concentration-time curve". For example, the AUC value of GIBH-1006 is highest, so the bioavailability of GIBH-1006 is also maximal.

Cmax: the peak concentration refers to the maximum plasma-drug concentration on the concentration-time curve, i.e., the maximum serum concentration that a drug may achieve after the drug has been administrated. The peak concentration is closely related to clinical applications of a drug. The drug may have a conspicuous effect after the concentration of the drug reaches the peak concentration, while the drug may have a toxic response if the concentration of the drug is beyond a safe range. In addition, the peak concentration is also an important indicator for the measurement of preparation absorption and safety.

T½ (half life time): is the time required for the drug plasma concentration to decrease by 50%, reflecting the speed of elimination by biotransformation or excretion.

Tmax (Peak Time): time required for the curve of drug concentration in human plasma to reach the highest concentration (peak concentration). Short peak time indicates quick absorption and effect and short residence time; and long peak time indicates slow absorption and effect and long residence time. Tmax is an important index of drug application and preparation research.

BA (bioavailability): the speed and degree of absorption in the systemic circulation. BA is further divided into absolute bioavailability and relative bioavailability. The absolute bioavailability is a percentage of absorption of other forms and doses of this drug by organism when this drug is administrated intravenously and utilized 100%; and the relative bioavailability is a percentage of utilization of other forms of this drug when a certain form (for example, water preparation for oral administration) is unitized 100%.

Vd (apparent volume of distribution): a ratio of the amount of drugs in the body to the drug plasma concentration when the drugs reach a dynamic balance in the body. According to the plasma concentration (c), it is estimated a volume that the total amount (A) of administrated compounds would have to occupy, that is, Vd=A/c (unit mL or mL/kg (body weight)). The smaller the Vd is, the quicker the excretion is and the shorter the residence time is; instead, the larger the Vd is, the slower the excretion is and the longer the residence time is. Vd is a theoretical volume, not a specifically physiological volume in the body. However, Vd may reflect the degree of distribution of drugs or the degree of binding with macromolecules in the tissues.

The embodiments mentioned above are merely several implementations of the present invention. Although these embodiments have been described specifically and in details, these embodiments shall not be regarded as any limitation to the present patent. It should be noted that, those skilled in the art may make various variations and improvements without departing from the concept of the present invention, and those variations and improvements shall fall into the protection cope of the present invention. Therefore, the protection scope of the present invention is subject to the claims.

The invention claimed is:

1. A method for inhibiting COX-2, the method comprising:
contacting a COX-2 or a cell containing COX-2 with an effective amount of a compound of Formula (I):

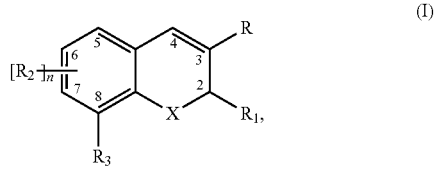

or a pharmaceutically acceptable salt thereof, wherein
X is selected from the group consisting of O, S, and NR$^a$,
R$^a$ is selected from the group consisting of H, $C_1$-$C_3$ alkyl, $C_3$-$C_6$ cycloalkyl, $C_1$-$C_3$ alkyl substituted with one or two halo, and aryl;
n is an integer selected from the group consisting of 1, 2, and 3;
R is selected from the group consisting of carboxyl, acylamino, alkylsulfonyl, and alkoxycarbonyl;

R₁ is selected from the group consisting of haloalkyl, alkyl, aralkyl, and cycloalkyl;

R₂ is selected from the group consisting of deuterium, halogen, alkyl, deuteroalkyl, aralkyl, deuteroaralkyl, haloalkyl, deuterohaloalkyl, alkoxy, deuteroalkoxy, aryloxy, deuteroaryloxy, heteroaryloxy, deutero-heteroaryloxy, arylalkoxy, deutero-arylalkoxy, heteroarylalkoxy, deutero-heteroarylalkoxy, haloalkoxy, deutero-haloalkoxy, amino, deuteroamino, sulfamidyl, and deuterosulfamidyl; and R₃ is deuteroalkyl.

2. The method of claim 1, wherein the cell is in a patient suffering from cancer.

3. The method of claim 2, wherein the cancer is selected from the group consisting of hemangioma, gastrointestinal stromal tumor, histiocytic lymphoma, non-small cell lung cancer, small-cell lung cancer, lung adenocarcinoma, squamous cell carcinoma, pancreatic cancer, breast cancer, prostate cancer, liver cancer, skin cancer, nasopharyngeal carcinoma, and leukemia.

4. The method of claim 3, wherein the cancer is selected from the group consisting of non-small cell lung cancer, lung adenocarcinoma, and squamous cell carcinoma, pancreatic cancer.

5. The method of claim 1, wherein the compound or salt is administered orally at a daily dose of 0.5-100 mg/day·kg.

6. The method of claim 5, wherein the compound or salt is administered at a daily dose of 1-100 mg/day·kg.

7. The method of claim 1, wherein the compound or salt is administered at a daily dose of 0.1 mg.

8. The method of claim 1, wherein
position 7 is unsubstituted;
X is O or S;
R is carboxyl, unsubstituted or aryl-substituted $C_1$-$C_3$ cyclocarbonyl, or $C_1$-$C_3$ alkoxycarbonyl;
R₁ is haloalkyl; and
each R₂ is independently selected from the group consisting of deuterium, halogen, alkyl, deuteroalkyl, haloalkyl, and deuterohaloalkyl.

9. The method of claim 8, wherein
n is selected from the group consisting of 1 and 2;
R is selected from the group consisting of carboxyl, unsubstituted or aryl-substituted $C_1$-$C_3$ cyclocarbonyl, and $C_1$-$C_3$ alkoxycarbonyl;
R₁ is selected from the group consisting of haloalkyl, cycloalkyl, and phenyl; and
R₂ is selected from the group consisting of deuterium, halogen, alkyl, deuteroalkyl, haloalkyl, deuterohaloalkyl, alkoxy, deuteroalkoxy, alkylamino, deuteroalkylamino, alkylated sulfamidyl, and alkylated deuterosulfamidyl,
wherein at least one R₂ is substituted at position 6 of the Formula (I) ring structure.

10. The method of claim 1, wherein X is O, R is —COOH, R₁ is trifluoromethyl, and at least one R₂ is halo.

11. The method of claim 1, wherein the compound is 8-(ethyl-D5)-6-(trifluoromethoxy)-2-(trifluoromethyl)-2H-chromene-3-carboxylic acid, or a salt thereof.

12. The method of claim 1, wherein the compound is 6-chloro-8-(methyl-D3)-2-(trifluoromethyl)-2H-chromene-3-carboxylic acid, or a salt thereof.

13. The method of claim 1, wherein the compound is 6-bromo-8-(methyl-D3)-2-(trifluoromethyl)-2H-chromene-3-carboxylic acid, or a salt thereof.

14. The method of claim 1, wherein the compound is 6,8-(dimethyl-D6)-2-(trifluoromethyl)-2H-chromene-3-carboxylic acid, or a salt thereof.

15. The method of claim 1, wherein the compound is 6-chloro-8-(1-methylhexyl-D15)-2-(trifluoromethyl)-2H-chromene-3-carboxylic acid, or a salt thereof.

16. The method of claim 1, wherein the compound is 7,8-(dimethyl-D6)-2-(trifluoromethyl)-2H-chromene-3-carboxylic acid, or a salt thereof.

17. The method of claim 1, wherein the compound is 6-chloro-8-(hexyl-D13)-2-(trifluoromethyl)-2H-chromene-3-carboxylic acid, or a salt thereof.

18. The method of claim 1, wherein the compound or salt is administered in a composition comprising at least one pharmaceutically acceptable carrier, excipient, or diluent.

* * * * *